US009879312B2

(12) United States Patent
Steemers et al.

(10) Patent No.: US 9,879,312 B2
(45) Date of Patent: Jan. 30, 2018

(54) SELECTIVE ENRICHMENT OF NUCLEIC ACIDS

(71) Applicant: ILLUMINA, INC., San Diego, CA (US)

(72) Inventors: Frank J. Steemers, Encinitas, CA (US); Kevin Gunderson, Encinitas, CA (US); Kerri York, San Diego, CA (US); Melissa Shults Won, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/150,716

(22) Filed: May 10, 2016

(65) Prior Publication Data

US 2016/0289742 A1   Oct. 6, 2016

Related U.S. Application Data

(62) Division of application No. 13/984,005, filed as application No. PCT/US2011/024091 on Feb. 8, 2011, now Pat. No. 9,365,897.

(51) Int. Cl.
*C12Q 1/68* (2006.01)

(52) U.S. Cl.
CPC ......... *C12Q 1/6806* (2013.01); *C12Q 1/6869* (2013.01)

(58) Field of Classification Search
None
See application file for complete search history.

(56) References Cited

U.S. PATENT DOCUMENTS

| | | | |
|---|---|---|---|
| 4,599,303 A | 7/1986 | Yabusaki et al. |
| 4,683,195 A | 7/1987 | Mullis et al. |
| 4,683,202 A | 7/1987 | Mullis |
| 4,800,159 A | 1/1989 | Mullis et al. |
| 4,826,967 A | 5/1989 | Glass |
| 4,883,750 A | 11/1989 | Whiteley et al. |
| 4,965,188 A | 10/1990 | Mullis et al. |
| 5,034,506 A | 7/1991 | Summerton et al. |
| 5,082,934 A | 1/1992 | Saba |
| 5,210,015 A | 5/1993 | Gelfand et al. |
| 5,399,491 A | 3/1995 | Kacian et al. |
| 5,432,272 A | 7/1995 | Benner |
| 5,476,930 A | 12/1995 | Letsinger et al. |
| 5,593,826 A | 1/1997 | Fung et al. |
| 5,721,099 A | 2/1998 | Still et al. |
| 5,854,033 A | 12/1998 | Lizardi |
| 5,858,412 A | 1/1999 | Staniforth et al. |
| 5,866,337 A | 2/1999 | Schon |
| 5,871,921 A | 2/1999 | Landegren et al. |
| 6,005,093 A | 12/1999 | Wood et al. |
| 6,174,670 B1 | 1/2001 | Wittwer et al. |
| 6,235,472 B1 | 5/2001 | Landegren et al. |
| 6,287,824 B1 | 9/2001 | Lizardi |
| 6,858,412 B2 | 2/2005 | Willis et al. |
| 7,582,420 B2 | 9/2009 | Oliphant |
| 9,365,897 B2 * | 6/2016 | Steemers ............. C12Q 1/6806 |
| 2003/0054360 A1 * | 3/2003 | Gold ................. C12N 15/1048 435/6.11 |
| 2003/0138800 A1 | 7/2003 | Van Ness et al. |
| 2004/0166529 A1 | 8/2004 | Singh et al. |
| 2006/0024711 A1 | 2/2006 | Lapidus et al. |
| 2008/0213860 A1 | 9/2008 | Xu et al. |
| 2008/0286775 A1 * | 11/2008 | Becker ................ C12Q 1/6806 435/6.11 |
| 2009/0011514 A1 | 1/2009 | Williams et al. |
| 2010/0022761 A1 | 1/2010 | Chen et al. |
| 2010/0311064 A1 | 12/2010 | Oliphant et al. |

OTHER PUBLICATIONS

Dahl F et al. "Multiplex amplification and massively parallel sequencing for cancer mutation discovery," Proc. Natl. Sci. USA 104:9387-9392 (2007).
Dahl, F et al. "Multiplex amplification enabled by selective circularization of large sets of genomic DNA fragments," Nucleic Acids Res. 33:e71; (2005).
Dapprich et al., "SNP-specific extraction of haplotype-resolved targeted genomic regions," Nucleic Acid Res. 36(15):e94 (2008).
Demidov et al., "Duplex DNA capture," Curr. Issues Mol. Biol. 2:31-35 (2000).
Demidov et al., "Kinetics and mechanism of the DNA double helix invasion by pseudocomplementary peptide nucleic acids," Proc. Natl. Acad. Sci. 99:5953-58 (2002).
Denny W.A. ed., " New developments in the use of nitrogen mustard alkylating agents as anticancer drugs," in "Advances in DNA Sequence-Specific Agents" series, Eds. Graham B. Jones and Manlio Palumbo, JAI Press v.3:157 (1998).
Faham M, et al. "Mismatch repair detection (MRD): high throughput scanning for DNA variations," Hum Mol Genet. 10(16): 657-64 (2001).
Fakhrai-Rad H, et al., "SNP Discovery in Pooled Samples with Mismatch Repair Detection," Genome Res.14(7):1404-12 (2004).
Goodchild, J., "Conjugates of Oligonucleotides and Modified Oligonucleotides: A Review of their Synthesis and Properties," Bioconj. Chem. 1:165-87 (1990).
Hakvoort B.M. et al., "Preparation of a differentially expressed, full-length cDNA expression library by RecA-mediated triple-strand formation with subtractively enriched cDNA fragments," Nucleic Acids Research 24:3478-3480 (1996).
Hardenbol et al., "Highly multiplexed molecular inversion probe genotyping: Over 10,000 targeted SNPs genotyped in a single tube assay," Genome Res. 15(2):269-275 (2005).
Hardenbol, P. et al., "Multiplexed genotyping with sequence-tagged molecular inversion probes," Nature Biotechnology 21 (6): 673-678 (2003).
International Search Report dated Aug. 1, 2011 received in International Application No. PCT/US2011/24091.
Ito et al., "Sequence-specific DNA purification by triplex affinity capture," Proc. Natl. Acad. Sci. 89:495-498 (1992).
Jain, M, et al., "Definitive Studies of Genetic Association," Genetic Engineering News 24(18):34-35 (2004).
Kandpal RP., et al., "Selective enrichment of a large size genomic DNA fragment by affinity capture: an approach for genome mapping." Nucleic Acids Research 18:1789-1795 (1990).
Krishnakumar S, et al., "A comprehensive assay for targeted multiplex amplification of human DNA sequences," Proc. Natl. Acad. Sci. USA 105:9296-9301 (2008).

(Continued)

*Primary Examiner* — James Martinell

(57) ABSTRACT

Methods for the selective enrichment of nucleic acids.

19 Claims, 9 Drawing Sheets

(56) References Cited

OTHER PUBLICATIONS

Nilsson,M. et al., "Padlock Probes: Circularizing Oligonucleotides for Localized DNA Detection," Science 265: 2085-88 (1994).
Porreca, GJ et al. "Multiplex amplification of large sets of human exons," Nat. Methods. 4(11):931-936 (2007).
Shepard AR. et al. "Magnetic bead capture of cDNAs from double-stranded plasmid cDNA libraries," Nucleic Acids Research 25:3183-3185 (1997).
Sonti S.Y. et al., "Large scale isolation of expression vector cassette by magnetic triple helix affinity capture," Nucleic Acids Research 23:3995-3996 (1995).
Takasugi M, et al. Sequence-Specific Photo-Induced Crosslinking of the Two Strands of Double-Helical DNA by a Psoralen Covalently Linked to a Triple Helix-Forming Oligonucleotide. Proc. Natl. Acad. USA 88:S602-S606 (1991).

* cited by examiner

SELECTIVE ENRICHMENT OF NUCLEIC ACIDS

RELATED APPLICATIONS

This application is a divisional of U.S. Ser. No. 13/984,005 filed Aug. 6, 2013 which is the U.S. National Phase of PCT Application No. PCT/US2011/024091 entitled "SELECTIVE ENRICHMENT OF NUCLEIC ACIDS" filed Feb. 8, 2011, and published in English on Aug. 16, 2012 as WO 2012/108864 the disclosure of each is incorporated herein by reference in its entirety.

REFERENCE TO SEQUENCE LISTING

The present application is being filed along with a Sequence Listing in electronic format. The Sequence Listing is provided as a file entitled SEQLISTILLINC137D1.TXT, created May 10, 2016, which is approximately 1.5 Kb in size. The information in the electronic format of the Sequence Listing is incorporated herein by reference in its entirety

FIELD OF THE INVENTION

Embodiments of the present invention relate to the fields of biology and genomics. More particularly, the present invention relates to the selective enrichment of nucleic acids.

BACKGROUND

Large-scale sequence analysis of genomic DNA is central to understanding a wide range of biological phenomena related to health and disease in humans and in economically important plants and animals. The need for low-cost, high-throughput sequencing and re-sequencing has led to the development of new approaches to sequencing that employ parallel analysis of many target DNA fragments simultaneously. Improvements to sequencing methods and increasing the amount and quality of data from such methods are of great value.

SUMMARY

Some embodiments of the present invention relate to methods and compositions for the selective enrichment of nucleic acids. Some embodiments include the selective enrichment of long nucleic acids comprising a target nucleic acid. Some embodiments include the selective enrichment of PCR products.

Some embodiments of the methods described herein comprise (a) contacting the population of nucleic acids with a nickase, thereby producing a population of nicked nucleic acids; (b) contacting the population of nicked nucleic acids with an exonuclease, thereby generating a nucleic acid having a single-stranded portion, wherein the single-strand portion comprises at least a portion of the target; (c) contacting a capture probe to the at least a portion of the target, wherein the probe hybridizes to the target; and (d) separating a nucleic acid hybridized to the capture probe from a nucleic acid not bound to the capture probe.

In other embodiments, the methods comprise (a) obtaining a population of nucleic acids, wherein at least some of the nucleic acids in the population comprise a target; (b) contacting the population of nucleic acids with a nickase, thereby producing a population of nicked nucleic acids; (c) contacting the population of nicked nucleic acids with an exonuclease, thereby generating a nucleic acid having a single-stranded portion, wherein the single-strand portion comprises at least a portion of the target; (d) contacting a capture probe to the at least a portion of the target, wherein the probe hybridizes to the target; and (e) separating a nucleic acid hybridized to the capture probe from a nucleic acid not bound to the capture probe.

Some embodiments of the methods described herein also include a step of releasing the hybridized nucleic acid from the capture probe. Other embodiments also include amplifying the target. Still further embodiments additionally include sequencing at least a portion of the target.

In some preferred embodiments of the methods described herein, the obtaining step also includes selecting for a population of nucleic acids having an average length greater than about 10 kb.

In other preferred embodiments of the methods described herein, one or more process steps, for example step (a), can also include contacting the population of double stranded nucleic acids with a type II restriction endonuclease that includes an isoschizomer of the nickase; and recircularizing the cut double stranded nucleic acids under conditions that favor intramolecular recircularization of individual nucleic acids. In such embodiments, various type II restriction endonucleases, or combinations of type II restriction endonucleases, can be used. In some embodiments, for example, the restriction endonuclease includes BbvCI. In other embodiments, the nickase includes Nb.BbvCI and Nt.BbvCI.

In some embodiments of the methods described herein, the probe includes a capture moiety. In some such embodiments, the capture moiety includes biotin or streptavidin.

In some embodiments, the step of separating a nucleic acid hybridized to the capture probe from a nucleic acid not bound to the capture probe also includes contacting the hybridized target and probe to a binding moiety. In some embodiments, the binding moiety includes avidin, and streptavidin. In some embodiments, the binding moiety also includes a bead, microsphere or other particle.

Probes used in the methods described herein can include various types of molecules. In preferred embodiments, the probe comprises a nucleic acid. In some embodiments, the probe includes RNA.

Embodiments of the methods described herein also include repeating one or more steps of the process. In certain embodiments, all of the method steps are repeated.

In some embodiments of the methods described herein, the target includes a first capture moiety, and the probe includes a second capture moiety. Some such embodiments also include contacting the first capture moiety to a first binding moiety, thereby providing for enrichment of the target, and contacting the second capture moiety to a second binding moiety, thereby providing for enrichment of the probe.

In addition to the foregoing, some embodiments of the methods described herein also provide for the selective enrichment of a nucleic acid that comprise the steps of (a) providing a population of nucleic acids, wherein at least some of the nucleic acids in the population include a target hybridized with a capture probe; (b) locking the hybridized probe to the target; and (c) separating a nucleic acid locked to a probe from a nucleic acid that is not locked to a probe.

In other embodiments, the methods comprise (a) obtaining a population of nucleic acids, wherein at least some of the nucleic acids in the population include a target; (b) hybridizing the target with a capture probe; (c) locking the probe hybridized probe to the target; and (d) separating a nucleic acid locked to a probe from a nucleic acid that is not locked to a probe.

Additional embodiments described herein also include the step of releasing the nucleic acid locked to the capture probe. Other embodiments also include amplifying the target. Still further embodiments additionally include sequencing at least a portion of the target.

In some embodiments of the enrichment methods described herein, the obtaining step also includes obtaining a population of nucleic acids having an average length greater than about 10 kb.

In further embodiments of the methods described herein, capture probes hybridized to targets can be locked in various different ways. For example, in some embodiments, the locking includes contacting psoralen to the capture probe hybridized to the target.

In some embodiments of the methods described herein, the target includes a 5' portion and a 3' portion; the probe includes a C-loop probe comprising a first end complementary to at least a portion of the 5' portion of the target, an intermediary region, and a second end complementary to at least a portion of the 3' portion of the target; and the locking includes joining together the first end to the second end of the probe, thereby locking the probe to the target.

In additional embodiments, joining includes extending and ligating the first end to the second end of the probe. In still further embodiments, the extending incorporates a capture moiety into the probe.

In some embodiments of the methods described herein, the population of nucleic acids includes circularized nucleic acids.

In some embodiments of the methods described herein, the probe includes a capture moiety. In some such embodiments, the capture moiety includes biotin or streptavidin.

In some embodiments, the step of separating also includes contacting the hybridized target and probe to a binding moiety. In some embodiments, the binding moiety includes avidin and streptavidin. In some embodiments, the binding moiety also includes a bead, microsphere or other particle.

Probes used in the methods described herein can include various types of molecules including, but not limited to, nucleic acids. In preferred embodiments, the probe comprises a nucleic acid. In some embodiments, the probe includes RNA.

Embodiments of the methods described herein also include repeating one or more steps of the process. In certain embodiments, all of the method steps are repeated.

In some embodiments of the methods described herein, the target includes a first capture moiety, and the probe includes a second capture moiety. Some such embodiments also include contacting the first capture moiety to a first binding moiety, thereby providing for enrichment of the target, and contacting the second capture moiety to a second binding moiety, thereby providing for enrichment of the probe.

In addition to the foregoing, some embodiments of the methods described herein, also include methods for selective enrichment of a nucleic acid that comprise (a) providing a population of nucleic acids, wherein at least some of the nucleic acids in the population include a target that comprises a portion of the 5' end of a nucleic acid and a portion of the 3' end of the nucleic acid, said target being hybridized to a selector probe that comprises a first and second oligonucleotide annealed together, wherein the first oligonucleotide is complementary to at least a portion of the 5' end of the nucleic acid and complementary to at least a portion of the second oligonucleotide, and the second oligonucleotide is complementary to at least a portion of the 3' end of the nucleic acid; (b) joining the selector probe to the target; and (c) separating a nucleic acid joined to the selector probe from a nucleic acid not joined to the selector probe.

Other embodiments of the enrichment methods described herein comprise the steps of (a) obtaining a population of nucleic acids, wherein at least some of the nucleic acids in the population include a target, the target including a portion of the 5' end of a nucleic acid and a portion of the 3' end of the nucleic acid; (b) obtaining a selector probe that comprises a first and second oligonucleotide annealed together, wherein the first oligonucleotide is complementary to at least a portion of the 5' end of the nucleic acid and complementary to at least a portion of the second oligonucleotide, and the second oligonucleotide is complementary to at least a portion of the 3' end of the nucleic acid; (c) contacting the selector probe to the target, wherein the probe hybridizes to the target; (d) joining the selector probe to the target; and (e) separating a nucleic acid joined to the selector probe from a nucleic acid not joined to the selector probe.

Additional embodiments described herein also include the step of releasing the nucleic acid joined to the selector probe. Other embodiments also include amplifying the target. Still further embodiments additionally include sequencing at least a portion of the target.

In some embodiments of the enrichment methods described herein, the obtaining step also includes obtaining a population of nucleic acids having an average length greater than about 10 kb.

In further embodiments of the methods described herein, the probe and target are contacted with Rec A.

In some embodiments of the methods described herein, the probe includes a capture moiety. In some such embodiments, the capture moiety includes streptavidin.

In some embodiments, the step of separating also includes contacting a binding moiety to the probe joined to the target. In some embodiments, the binding moiety includes avidin and streptavidin. In some embodiments, the binding moiety also includes a bead, microsphere or other particle.

Probes used in the methods described herein can include various types of molecules including, but not limited to, nucleic acids. In preferred embodiments, the probe comprises a nucleic acid. In some embodiments, the probe includes RNA.

Embodiments of the methods described herein also include repeating one or more steps of the process. In certain embodiments, all of the method steps are repeated.

In some embodiments of the methods described herein, the target includes a first capture moiety, and the probe includes a second capture moiety. Some such embodiments also include contacting the first capture moiety to a first binding moiety, thereby providing for enrichment of the target, and contacting the second capture moiety to a second binding moiety, thereby providing for enrichment of the probe.

In addition to the foregoing, some embodiments of the methods described herein also include methods for selective enrichment of a nucleic acid that comprise (a) providing a population of single-stranded nucleic acids, wherein at least some of the nucleic acids in the population include a target, the target comprising the 5' end of a nucleic acid and the 3' end of the nucleic acid, said target being hybridized to a selector probe that comprises a first and second oligonucleotide annealed together, wherein the first oligonucleotide comprises a 5' portion complementary to the 3' end of the nucleic acid, a spacer portion, and a 3' portion complementary to the 5' end of the nucleic acid, the second oligonucleotide being complementary to the spacer portion; (b) joining the selector probe to the target; and (c) separating a nucleic acid joined to the selector probe from a nucleic acid not joined to the selector probe.

Other embodiments of the methods described herein comprise (a) obtaining a population of single-stranded nucleic acids, wherein at least some of the nucleic acids in the population include a target, the target comprising the 5' end of a nucleic acid and the 3' end of the nucleic acid; (b) obtaining a selector probe that includes a first and second oligonucleotide annealed together, wherein the first oligonucleotide comprises a 5' portion complementary to the 3' end of the nucleic acid, a spacer portion, and a 3' portion complementary to the 5' end of the nucleic acid, the second oligonucleotide being complementary to the spacer portion; (c) contacting the selector probe to the target, wherein the probe hybridizes to the target; (d) joining the selector probe to the target; and (e) separating a nucleic acid joined to the selector probe from a nucleic acid not joined to the selector probe.

In some embodiments, one end of the selector probe has an annealing temperature different from the other end.

Additional embodiments described herein also include the step of releasing the nucleic acid joined to the selector probe. Other embodiments also include amplifying the target. Still further embodiments additionally include sequencing at least a portion of the target.

In some embodiments of the enrichment methods described herein, the obtaining step also includes obtaining a population of nucleic acids having an average length greater than about 10 kb.

In some embodiments of the methods described herein, the probe includes a capture moiety. In some such embodiments, the capture moiety includes biotin or streptavidin.

In some embodiments, the step of separating also includes contacting the hybridized target and probe to a binding moiety. In some embodiments, the binding moiety includes avidin and streptavidin. In some embodiments, the binding moiety also includes a bead, microsphere or other particle.

Probes used in the methods described herein can include various types of molecules including, but not limited to, nucleic acids. In preferred embodiments, the probe comprises a nucleic acid. In some embodiments, the probe includes RNA.

Embodiments of the methods described herein also include repeating one or more steps of the process. In certain embodiments, all of the method steps are repeated.

In some embodiments of the methods described herein, the target includes a first capture moiety, and the probe includes a second capture moiety. Some such embodiments also include contacting the first capture moiety to a first binding moiety, thereby providing for enrichment of the target, and contacting the second capture moiety to a second binding moiety, thereby providing for enrichment of the probe.

In addition to the foregoing, some embodiments of the present invention also include methods for normalizing amplified nucleic acids that include selecting a first population of oligonucleotides having a ratio of oligonucleotides that includes capture moieties to oligonucleotides lacking capture moieties for a first population of oligonucleotides; obtaining a second population of oligonucleotides; amplifying target nucleic acids with the first and second populations of oligonucleotides; and separating amplified targets having incorporated oligonucleotide comprising capture moieties from amplified targets lacking incorporated oligonucleotide capture moieties.

In some embodiments, the capture moiety is selected from biotin or streptavidin.

In some embodiments, the step of separating further comprises contacting the hybridized target and probe to a binding moiety. In some embodiments, the binding moiety includes avidin and streptavidin. In some embodiments, the binding moiety also includes a bead, microsphere or other particle.

DETAILED DESCRIPTION

Some embodiments of the present invention relate to methods and compositions for the selective enrichment of nucleic acids. Some embodiments include the selective enrichment of long nucleic acids comprising a target nucleic acid. Some embodiments include the selective enrichment of PCR products.

Selective enrichment of long nucleic acids provides several advantages in applications such as nucleic acid sequencing. For example, some methods of sequencing utilize libraries of sequencing elements. In many conventional libraries, each sequencing element can comprise a nucleic acid of approximately 250 bp. To sequence a 0.5 Mb region of a genome using such a conventional library, at least 2000 probes would be required. In contrast, a library comprising sequencing elements of at least 10 kb would require 50 probes or less to sequence 0.5 Mb. Accordingly, a library of sequencing elements comprising long nucleic acids would greatly enhance the efficiency of certain applications, such as certain nucleic acid sequencing methods.

However, enriching a mixture of long nucleic acids from a source such as genomic DNA presents several challenges. For example, some types of genomic DNA, such as human genomic DNA contain many regions comprising repetitive elements. Repetitive elements include, but are not limited to, tandem repeats, e.g., satellite DNA, minisatellites and microsatellites, and interspersed repeats, e.g., SINEs (short interspersed nuclear elements) and LINEs (long interspersed nuclear elements). Some such repetitive elements readily hybridize to each other when double-stranded genomic DNA is denatured to single-stranded DNA.

Some of the methods and compositions provided herein to enrich for long nucleic acids comprising a target nucleic acid include methods in which cross-hybridization of repetitive elements is minimized. For example, in some methods a capture probe hybridizes to double-stranded nucleic acids. In some such methods, a triple helix may be formed.

Some of the methods and compositions provided herein to enrich for long nucleic acids comprising a target nucleic acid include methods in which a capture probe and target nucleic acid are strongly associated together. For example, in some methods provided herein, a capture probe and target nucleic acid can be covalently associated with each other. In another example, a capture probe and target nucleic acid can be topologically linked to each other. In another example, a capture probe can be integrated into a long nucleic acid comprising a target nucleic acid. In some methods, in which a capture probe and target nucleic acid are strongly associated together, the stringency of washing steps can be greatly increased to remove unassociated capture probe and unassociated nucleic acids from the capture probes associated with nucleic acids comprising target nucleic acids.

Figure 1:
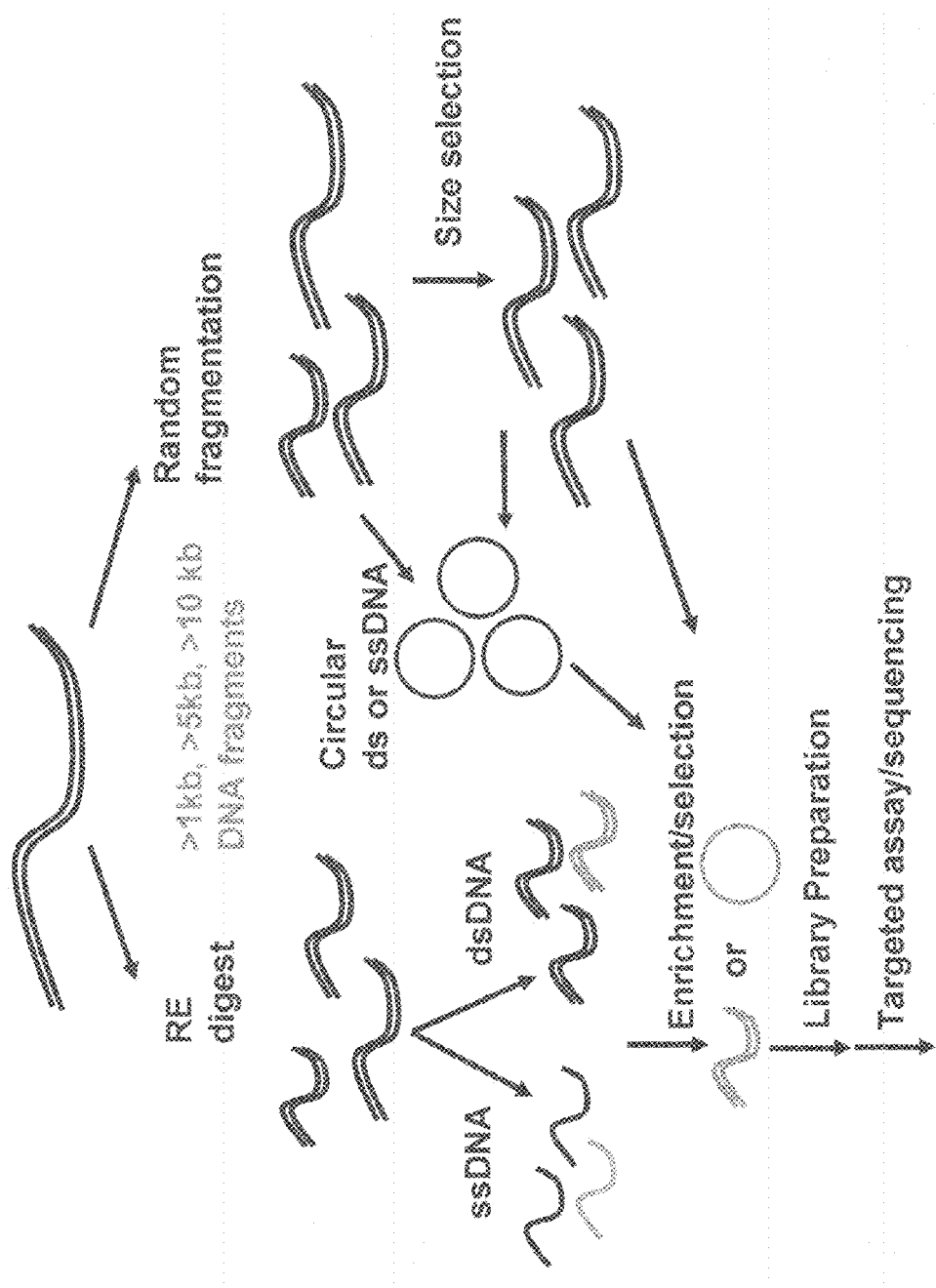
FIG. 1 shows a schematic diagram summarizing some embodiments that include restriction endonuclease (RE) digestion or random fragmentation of DNA to yield a mixture of nucleic acids with average lengths of greater than 1 kb, greater than 5 kb, or greater than 10 kb. In one pathway, fragmented nucleic acids may undergo circularization to dsDNA or ssDNA and/or size selection. Circularized DNA or size-selected DNA may undergo enrichment/selection. In another pathway, ssDNA or dsDNA may undergo enrichment/selection.

Long nucleic acids can be further enriched by binding capture probes associated with target nucleic acids to binding moieties. For example, a capture probe can include an affinity tag (e.g., biotin) that binds to a binding moiety, e.g., avidin or streptavidin. In some embodiments, long nucleic acids comprising a target nucleic acid can be further processed. For example, long nucleic acids prepared using the methods described herein can be circularized and amplified using methods such as circle-dependent replication (CDR). In some methods, amplified long nucleic acids can be used to prepared library templates for nucleic acid sequencing. FIG. 1 provides an overview of some embodiments provided herein.

Definitions

As used herein, the terms "polynucleotide", "oligonucleotide", "nucleic acid", and "nucleic acid sequence" are generally used interchangeably and include single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, tetraalkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotide analogs. Nucleic acids typically range in size from a few monomeric units, e.g. 5-40 when they are sometimes referred to in the art as oligonucleotides, to several thousands of monomeric nucleotide units. Nucleic acid sequence are shown in the 5' to 3' orientation from left to right, unless otherwise apparent from the context or expressly indicated differently; and in such sequences, "A" denotes deoxyadenosine, "C" denotes deoxycytidine, "G" denotes deoxyguanosine, "T" denotes thymidine, and "U" denotes uridine. Nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample. Nucleic acids may be composed of a single type of sugar moiety, e.g., as in the case of RNA and DNA, or mixtures of different sugar moieties, e.g., as in the case of RNA/DNA chimeras.

The term "nucleotide analogs" refers to synthetic analogs having modified nucleotide base portions, modified pentose portions, and/or modified phosphate portions, and, in the case of polynucleotides, modified internucleotide linkages, as generally described elsewhere (e.g., Scheit, *Nucleotide Analogs*, John Wiley, New York, 1980; Englisch, *Angew. Chem. Int. Ed. Engl.* 30:613-29, 1991; Agarwal, *Protocols for Polynucleotides and Analogs*, Humana Press, 1994; and S. Verma and F. Eckstein, Ann. Rev. Biochem. 67:99-134, 1998). Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, S-Me-Bz-C-LNA, dmf-G-LNA, and T-LNA (see, e.g., The Glen Report, 16(2): 5, 2003; Koshkin et al., *Tetrahedron* 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., Organic Chem., 52:4202, 1987), and uncharged morpholino-based polymers having achiral intersubunit linkages (see, e.g., U.S. Pat. No. 5,034,506). Some internucleotide linkage analogs include morpholidate, acetal, and polyamide-linked heterocycles. In one class of nucleotide analogs, known as peptide nucleic acids, including pseudocomplementary peptide nucleic acids ("PNA"), a conventional sugar and internucleotide linkage has been replaced with a 2-aminoethylglycine amide backbone polymer (see, e.g., Nielsen et al., Science, 254:1497-1500, 1991; Egholm et al., J. Am. Chem. Soc., 114: 1895-1897 1992; Demidov et al., *Proc. Natl. Acad. Sci.* 99:5953-58, 2002; Peptide Nucleic Acids: Protocols and Applications, Nielsen, ed., Horizon Bioscience, 2004). The term "$T_m$ enhancing nucleotide analog" as used herein refers to a nucleotide analog that, when incorporated into a primer or extension product, increases the annealing temperature of that primer or extension product relative to a primer or extension product with the same sequence comprising conventional nucleotides (A, C, G, and/or T), but not the $T_m$ enhancing nucleotide analog. Those in the art will appreciate that Tm can be determined experimentally using well-known methods or can be estimated using algorithms, thus one can readily determine whether a particular nucleotide analog will serve as a Tm enhancing nucleotide analog when used in a particular context, without undue experimentation. A wide range of nucleotide analogs are available as triphosphates, phoshoramidites, or CPG derivatives for use in enzymatic incorporation or chemical synthesis from, among other sources, Glen Research, Sterling, Md.; Link Technologies, Lanarkshire, Scotland, UK; and TriLink BioTechnologies, San Diego, Calif. Descriptions of oligonucleotide synthesis and nucleotide analogs, can be found in, among other places, S. Verma and F. Eckstein, Ann. Rev. Biochem. 67:99-134 (1999); Goodchild, Bioconj. Chem. 1:165-87 (1990); Current Protocols in Nucleic Acid Chemistry, Beaucage et al., eds., John Wiley & Sons, 1999, including supplements through January 2005; and Nucleic Acids in Chemistry and Biology, 2d ed., Blackburn and Gait, eds., Oxford University Press, 1996.

As used herein the term "complementary" and grammatical equivalents refer to the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which hybridization tags anneal to complementary or substantially complementary regions of target nucleic acids well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the hybridizing region of the hybridization tags and their complementary sequences, the pH, the temperature, the presence of mono- and divalent cations, the proportion of G and C nucleotides in the hybridizing region, the viscosity of the medium, and the presence of denaturants. Such variables influence the time required for hybridization. The presence of certain nucleotide analogs or groove binders in the hybridization tags can also influence hybridization conditions. Thus, the preferred annealing conditions will depend upon the particular application. Such conditions, however, can be routinely determined by persons of ordinary skill in the art, without undue experimentation. Typically, annealing conditions are selected to allow complementary or substantially complementary portions of hybridization tags to selectively hybridize with their corresponding target sequence, but not hybridize to any significant degree to other sequences in the reaction.

As used herein, the term "hybridization" refers to the process in which two single-stranded polynucleotides bind non-covalently to form a stable double-stranded polynucleotide. A resulting double-stranded polynucleotide is a "hybrid" or "duplex." Hybridization conditions will typically include salt concentrations of less than about 1 M, more usually less than about 500 mM and may be less than about 200 mM. A hybridization buffer includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Example stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of 30° C. are suitable for allele-specific probe hybridizations.

As used herein, the term "ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921, incorporated herein by reference in their entireties.

As used herein, the term "amplicon" can refer to the product of a polynucleotide amplification reaction, for example, a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle-dependent amplification and like reactions (see, e.g., U.S. Pat. Nos. 4,683,195; 4,965,188; 4,683,202; 4,800,159; 5,210,015; 6,174,670; 5,399,491; 6,287,824 and 5,854,033; and US Patent Application Publication No. 2006/0024711, incorporated herein by reference in their entireties).

As used herein, the term "circle-dependent replication" or "CDR" can refer to multiple displacement amplification of a double-stranded circular template using one or more primers annealing to the same strand of the circular template to generate products representing only one strand of the template. In CDR, no additional primer binding sites are generated and the amount of product increases only linearly with time. The primer(s) used may be of a random sequence (e.g., one or more random hexamers) or may have a specific sequence to select for amplification of a desired product. Without further modification of the end product, CDR often results in the creation of a linear construct having multiple copies of a strand of the circular template in tandem, i.e. a linear, single-stranded concatamer of multiple copies of a strand of the template.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), Genome Analysis: A Laboratory Manual Series (Vols. I-IV); Weiner, Gabriel, Stephens, Eds. (2007), Genetic Variation: A Laboratory Manual; Dieffenbach, Dveksler, Eds. (2003), PCR Primer: A Laboratory Manual; Bowtell and Sambrook (2003), DNA Microarrays: A Molecular Cloning Manual; Mount (2004), Bioinformatics: Sequence and Genome Analysis; Sambrook and Russell (2006), Condensed Protocols from Molecular Cloning: A Laboratory Manual; and Sambrook and Russell (2002), Molecular Cloning: A Laboratory Manual (all from Cold Spring Harbor Laboratory Press); Stryer, L. (1995) Biochemistry (4th Ed.) W.H. Freeman, New York N.Y.; Gait, "Oligonucleotide Synthesis: A Practical Approach" 1984, IRL Press, London; Nelson and Cox (2000), Lehninger, Principles of Biochemistry $3^{rd}$ Ed., W.H. Freeman Pub., New York, N.Y., all of which are herein incorporated in their entirety by reference for all purposes.

Target Nucleic Acids

Some embodiments described herein include the selective enrichment of a target nucleic acid. A target nucleic acid can include a single-stranded and/or a double-stranded nucleic acid. In some embodiments, a target can comprise at least a portion of a target nucleic acid. As used herein the term "at least a portion" and grammatical equivalents can refer to a value equivalent to any fraction of a whole, including a value equivalent to a whole. For example, "at least a portion" can refer to less than about, more than about and about 1%, about 5%, about 10%, about 20%, about 30%, about 40%, about 50%, about 60%, about 70%, about 80%, about 90%, about 95%, about 99%, and about 100%. In more embodiments, a target can comprise a sequence encoding a fragment of a target nucleic acid. A fragment can include two or more consecutive nucleotides. Some target nucleic acids can include one or more targets.

Target nucleic acids can include genomic nucleic acids, amplified nucleic acids, cloned nucleic acids, and the like. Examples of cloned nucleic acids include plasmids, cosmids, fosmids, YACs, and BACs. Genomic nucleic acids can be provided from sources such as cell cultures, tissues, and organisms. Nucleic acids, e.g., genomic nucleic acids, can include sequences such as coding sequences, non-coding sequences, control elements, and repetitive elements such interspersed repetitive elements e.g., LINEs, SINEs, LTRs, and DNA transposons, and tandem repeats.

In some embodiments, target nucleic acids can include long nucleic acids. Long nucleic acids can comprise a length of at least about 1 kb, at least about 5 kb, at least about 10 kb, at least about 20 kb, at least about 30 kb, at least about 40 kb, at least about 50 kb, at least about 60 kb, at least about 70 kb, at least about 80 kb, at least about 90 kb, and at least about 100 kb. Long nucleic acids can also include nucleic acids that comprise a length of at least about 100 kb, at least about 200 kb, at least about 300 kb, at least about 400 kb, at least about 500 kb, at least about 600 kb, at least about 700 kb, at least about 800 kb, at least about 900 kb, and at least about 1000 kb.

Long nucleic acids can be prepared from sources by a variety of methods well known in the art. Methods for obtaining biological samples and subsequent nucleic acid isolation from such samples that maintain the integrity (i.e., minimize the breakage or shearing) of nucleic acid molecules are preferred. Exemplary methods include, but are not limited to, lysis methods without further purification (e.g., chemical or enzymatic lysis method using detergents, organic solvents, alkaline, and/or proteases), nuclei isolation with or without further nucleic acid purification, isolation methods using precipitation steps, nucleic acid isolation methods using solid matrices (e.g., silica-based membranes, beads, or modified surfaces that bind nucleic acid molecules), gel-like matrices (e.g., agarose) or viscous solutions, and methods that enrich nucleic acid molecules with a density gradient. Nucleic acids can be fragmented for use in some of the methods and compositions described herein by physical shearing, sonication, restriction digestion, and the like.

Capture Probes

Some of the methods and compositions described herein can utilize capture probes. In some embodiments, a capture probe can comprise one or more hybridization tags. As used herein, the term "hybridization tag" and grammatical equivalents can refer to a nucleic acid comprising a sequence complementary to at least a portion of a target. The degree of complementarity between a hybridization tag and a corresponding target sequence can vary with the application. In some embodiments, the hybridization tag can be complementary or substantially complementary to a target sequence or portions thereof. For example, a hybridization tag can comprise a sequence having a complementarity to a corresponding target sequence of at least about 50%, at least about 60%, at least about 70%, at least about 80%, at least about 90%, and at least about 99%. In some embodiments, a hybridization tag can comprise a sequence having 100% complementarity to a corresponding target sequence.

In some embodiments, a capture probe can include a plurality of hybridization tags in which the targets are located in the same nucleic acid, or different nucleic acids. In certain embodiments, hybridization tags comprising RNA may be advantageous to efficiently remove excess levels of such tags.

In certain embodiments, a hybridization tag can comprise at least about 5 nucleotides, at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, and at least about 100 nucleotides.

In additional embodiments, a capture probe can include an affinity tag. Affinity tags can be useful for the bulk separation of target nucleic acids hybridized to hybridization tags. As used herein, the term "affinity tag" and grammatical equivalents can refer to a component of a multi-component complex, wherein the components of the multi-component complex specifically interact with or bind to each other. For example an affinity tag can include biotin that can bind streptavidin. Other examples of multiple-component affinity tag complexes include, ligands and their receptors, for example, avidin-biotin, streptavidin-biotin, and derivatives of biotin, streptavidin, or avidin, including, but not limited to, 2-iminobiotin, desthiobiotin, NeutrAvidin (Molecular Probes, Eugene, Oreg.), CaptAvidin (Molecular Probes), and the like; binding proteins/peptides, including maltose-maltose binding protein (MBP), calcium-calcium binding protein/peptide (CBP); antigen-antibody, including epitope tags, including c-MYC (e.g., EQKLISEEDL (SEQ ID NO: 1)), HA (e.g., YPYDVPDYA (SEQ ID NO: 2)), VSV-G (e.g., YTDIEMNRLGK (SEQ ID NO: 3)), HSV (e.g., QPELA-PEDPED (SEQ ID NO: 4)), V5 (e.g., GKPIPNPLLGLDST (SEQ ID NO: 5)), and FLAG Tag™. (e.g., DYKDDDDKG (SEQ ID NO: 6)), and their corresponding anti-epitope antibodies; haptens, for example, dinitrophenyl and digoxigenin, and their corresponding antibodies; aptamers and their corresponding targets; fluorophores and anti-fluorophore antibodies; and the like.

In certain embodiments, a capture probe can comprise a reporter moiety. As used herein, the term "reporter moiety" and grammatical equivalents can refer to any identifiable tag, label, or group. The skilled artisan will appreciate that many different species of reporter moieties can be used with the methods and compositions described herein, either individually or in combination with one or more different reporter moieties. In certain embodiments, a reporter moiety can emit a signal. Examples of signals fluorescent, a chemiluminescent, a bioluminescent, a phosphorescent, a radioactive, a calorimetric, or an electrochemiluminescent signals. Example reporter moieties include fluorophores, radioisotopes, chromogens, enzymes, antigens including epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer compatible reporter moieties, such as mass tags, charge tags, and isotopes. More reporter moieties that may be used with the methods and compositions described herein include spectral labels such as fluorescent dyes (e.g., fluorescein isothiocyanate, Texas red, rhodamine, and the like), radiolabels (e.g., $^3$H, $^{125}$I, $^{35}$S, $^{14}$C, $^{32}$P, $^{33}$P, etc.), enzymes (e.g., horse-radish peroxidase, alkaline phosphatase etc.) spectral calorimetric labels such as colloidal gold or colored glass or plastic (e.g. polystyrene, polypropylene, latex, etc.) beads; magnetic, electrical, thermal labels; and mass tags. Reporter moieties can also include enzymes (horseradish peroxidase, etc.) and magnetic particles. More reporter moieties include chromophores, phosphors and fluorescent moieties, for example, Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking to an element desirably detected in an apparatus or assay provided herein, or which can be modified to incorporate such functionalities include, e.g., dansyl chloride; fluoresceins such as 3,6-dihydroxy-9-phenylxanthydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminonaphthalene-6-sulfonate; ethidium bromide; stebrine; auromine-0,2-(9'-anthroyl)palmitate; dansyl phosphatidylethanolamine; N,N'-dioctadecyl oxacarbocyanine: N,N'-dihexyl oxacarbocyanine; merocyanine, 4-(3'-pyrenyl) stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis(2-methyl-5-phenyl-oxazolyl))benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-(p-(2benzimidazolyl)-phenyl)maleimide; N-(4-fluoranthyl)maleimide; bis(homovanillic acid); resazarin; 4-chloro7-nitro-2,1,3-benzooxadiazole; merocyanine 540; resorufin; rose bengal; 2,4-diphenyl-3(2H)-furanone, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Pat. No. 6,544,732, hereby incorporated by reference), pyrene, Malachite green, stilbene, Lucifer Yellow, Cascade Blue™, Texas Red, Cy dyes (Cy3, Cy5, etc.), Alexa dyes, phycoerythin, bodipy, and others described in the 6th Edition of the Molecular Probes Handbook by Richard P. Haugland, expressly incorporated by reference herein.

In some embodiments, a capture probe can be associated with a substrate. Examples of substrates include microspheres, planar surfaces, columns, and the like. By "microsphere" or "bead" or "particle" or grammatical equivalents herein is meant a small discrete particle. The composition of the substrate will vary on the application. Suitable compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used "Microsphere Detection Guide" from Bangs Laboratories, Fishers Ind. is a helpful guide. The beads need not be spherical; irregular particles may be used. In some embodiments, a substrate can comprises a metallic composition, e.g., ferrous, and may also comprise magnetic properties. An example embodiment utilizing magnetic beads includes capture probes comprising streptavidin-coated magnetic beads (Ito et al., (1992) "Sequence-specific DNA purification by triplex affinity capture." P.N.A.S. 89:495-498, incorporated by reference herein in its entirety). In addition, the beads may be porous, thus increasing the surface area of the bead available for association with capture probes. The bead sizes range from nanometers, i.e. 100 nm, to millimeters, i.e. 1 mm, with beads from about 0.2 μm to about 200 μm being preferred, and from about 0.5 to about 5 μm being particularly preferred, although in some embodiments smaller beads may be used.

In certain embodiments, a capture probe can comprise a cleavable moiety, for example, a cleavable linker. Cleavable moieties can include functional groups that can be cleaved by methods such as photolytically, chemically, thermally, or enzymatically cleaved. See, e.g., U.S. Pat. No. 5,721,099; U.S. Patent Publication No. 20040166529; U.S. Patent Publication No. 20100022761; and Greene et al., PROTECTIVE GROUPS IN ORGANIC SYNTHESIS, 2nd ed. Wiley, 1991, incorporated by reference in their entireties. Any moiety of a capture probe can comprise a cleavable moiety, e.g., affinity tag, hybridization tag, and/or reporter moiety. In some such embodiments, the cleavable moiety can be configured to release a target from a capture probe.

In some embodiments, release of a target from a capture probe may be desired after bulk separation of a capture probe and target.

Capture probes may be prepared by a variety of methods. In some embodiments capture probes may be prepared in situ. For example, affinity tags, reporter moieties, and/or cleavable moieties can be incorporated into a capture probe hybridized to a nucleic acid. In some such embodiments, a hybridization tag hybridized to a target nucleic acid may be extended with nucleotides or nucleotide analogs that can comprise affinity tags, reporter moieties, or cleavable nucleotides. Such embodiments can be useful in the SNP-specific extraction of haplotype-resolved targeted genomic regions. In some embodiments, haploid chromosomal regions flanking targeted SNPs can be enriched for by hybridizing and enzymatically elongating capture probes comprising hybridization tags, e.g., oligonucleotides with affinity tags, e.g., biotinylated nucleotides based on their selective binding to target nucleic acids, e.g., unique sequence elements that differentiate one allele from any other differing sequence. In some embodiments, the targeted genomic region is further enriched by separation methods including streptavidin-coated magnetic particles (Dapprich et al., (2008) N.A. Res. 36(15):e94, incorporated by reference in its entirety). Briefly, some methods include targeting and subsequent extraction. In targeting, a SNP-specific oligonucleotide is designed with its 3'-end sequence overlapping the targeted SNP. A diploid DNA sample is heat-denatured and the extraction oligo is hybridized to the target sequence. For heterozygous polymorphisms, the exact sequence of the extraction oligo will be matched only by one of the two alleles of the diploid sample. The bound extraction oligo is enzymatically elongated with biotinylated nucleotides, which results in highly efficient tagging of only the targeted allele. In extraction, the tagged allele is then captured, along with flanking genomic DNA, from the diploid sample by attachment to streptavidin-coated magnetic microparticles. The haploid DNA/magnetic particle complex is washed twice to remove nontargeted, nonspecifically bound DNA from the surface, leaving the targeted allele of interest isolated for further analysis.

Methods for Enriching Targets Associated with Probes

Some embodiments of the present invention include methods to enrich target nucleic acids associated with capture probes. In some such embodiments, a capture probe comprising a hybridization tag can be hybridized and/or associated with a target nucleic acid. In some embodiments, the associated and/or hybridized target nucleic acid and hybridized capture probe can be enriched from other unhybridized and/or unassociated nucleic acids.

In some embodiments, enrichment can include associating a capture probe with a binding moiety. Binding moieties can be associated with the affinity tags, and can include ligands for such affinity tags. Binding moieties may be attached to substrates. In some embodiments, enrichment can include removing unhybridized and/or unassociated nucleic acids from the associated and/or hybridized target nucleic acid and hybridized capture probe. Methods of removing can include, for example, washing. Methods of washing nucleic acids are well known in the art. Such methods can be applied to methods that include hybridizing target nucleic acids with capture probes. A variety of hybridization and washing conditions may be used including high, moderate and low stringency conditions; see for example Maniatis et al., Molecular Cloning: A Laboratory Manual, 2d Edition, 1989, and Short Protocols in Molecular Biology, ed. Ausubel, et al, the disclosure of which is incorporated herein by reference in its entirety. Stringent conditions include those that can be sequence-dependent and will be different in different circumstances. Longer sequences hybridize specifically at higher temperatures. An extensive guide to the hybridization of nucleic acids is found in Tijssen, Techniques in Biochemistry and Molecular Biology-Hybridization with Nucleic Acid Probes, "Overview of principles of hybridization and the strategy of nucleic acid assays" (1993), the disclosure of which is incorporated herein by reference in its entirety. Generally, stringent conditions can be selected to be about 5-10° C. lower than the thermal melting point ($T_m$) for the specific sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions include those in which the salt concentration is less than about 1.0 M sodium ion, for example, about 0.01 M to 1.0 M sodium ion concentration (or other salts) at pH 7.0 to 8.3 and the temperature is at least about 3° C. for short probes (e.g. 10 to 50 nucleotides) and at least about 6° C. for long probes (e.g. greater than 50 nucleotides). Stringent conditions may also be achieved with the addition of helix destabilizing agents such as formamide. The hybridization or washing conditions may also vary when a non-ionic backbone, i.e. PNA is used, as is known in the art.

Some methods to enrich target nucleic acids associated with capture probes can include dissociating the target nucleic acid from at least a portion of a capture probe. In some embodiments, dissociating the target nucleic acid from at least a portion of a capture probe can be performed subsequent to removing nucleic acids not associated with a capture probe. As will be understood, methods to disassociate target nucleic acids from at least a portion of a capture probes will vary according to the type of association between the target nucleic acid and capture probe. In some embodiments target nucleic acids can be disassociated from at least a portion of a capture probe by denaturing nucleic acids, e.g., by increasing temperature. In some embodiments, a target nucleic acid can be disassociated from at least a portion of a capture probe by cleaving a cleavable linker. In some embodiments, a target nucleic acid can be disassociated from at least a portion of a capture probe by digesting at least a portion of the capture probe, e.g., RNA capture probes can be digested with RNAse. Some embodiments also include removing at least a portion of a capture probe disassociated from a target nucleic acid from the disassociated target nucleic acid by methods well known in the art, e.g., washing.

Figure 2:
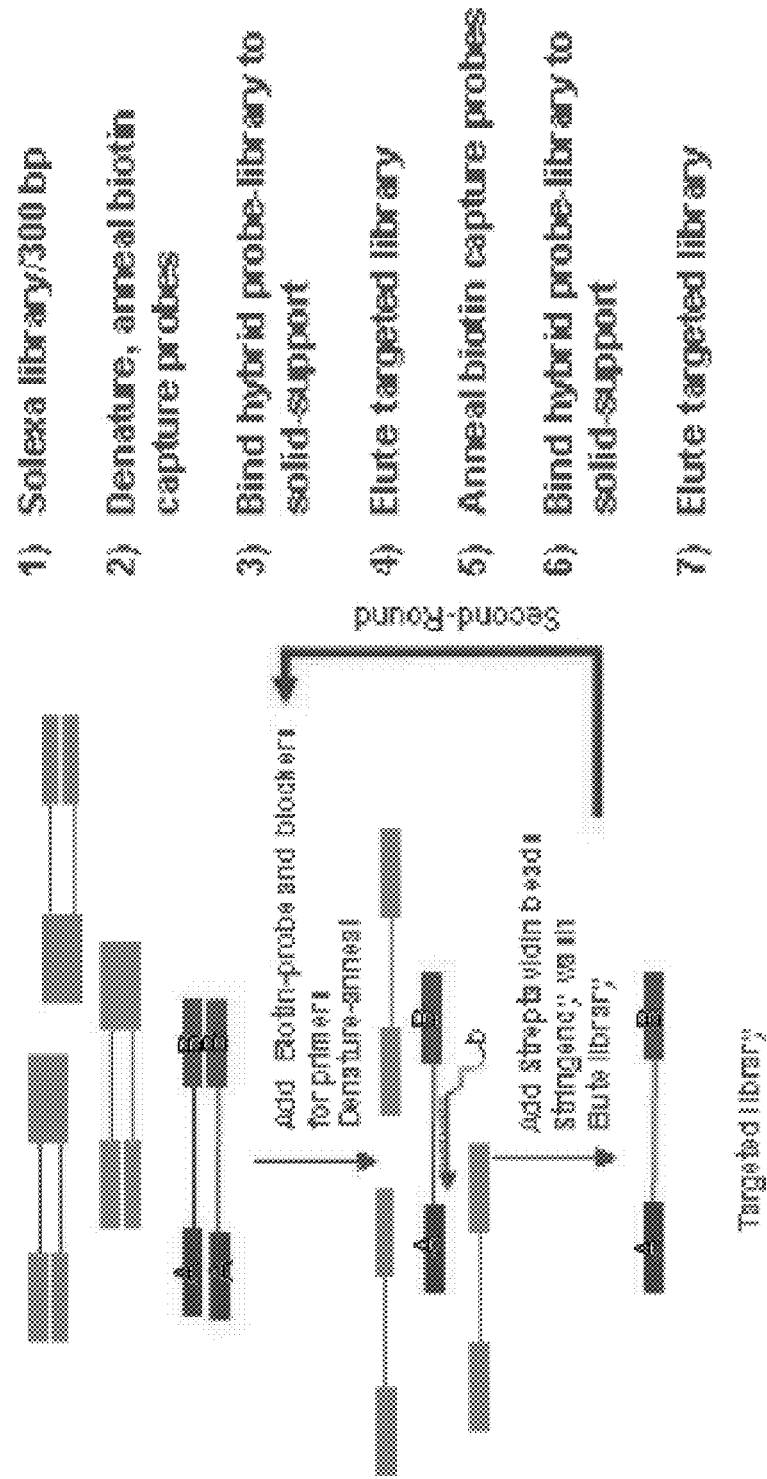
FIG. 2 shows a schematic diagram summarizing certain methods that include enrichment using biotin probes and more than one round of enrichment.

Some embodiments to enrich target nucleic acids associated with capture probes can include one or more rounds of enrichment. FIG. 2 summarizes an example embodiment that includes multiple rounds of a certain type of enrichment. The embodiment includes: (1) preparing a sequencing library comprising a mixture of nucleic acids; (2) denaturing the library and annealing biotin-labeled capture probes to nucleic acids comprising target nucleic acids (A, and B), (3) binding biotin-labeled capture probes and associated nucleic acids to a solid-support, e.g., magnetic streptavidin beads, (4) washing the beads and removing unassociated nucleic acids, and (5) eluting enriched nucleic acids comprising target nucleic acids from the beads. In the second round of enrichment, the enriched nucleic acids comprising target nucleic acids may undergo steps (2)-(5).

Some embodiments provided herein include solid-phase sequence libraries. Sequencing libraries can be tagged at the 5' portion with affinity ligands, allowing binding of the sequencing library to the solid-support at various stages in an assay. Advantage of such methods include the ability to expose sequencing libraries to high concentrations of capture probes thus increasing rates of hybridization, and allowing easy and quick removal of excess probes. Capturing libraries on solid-supports, especially in diluted form, minimizes library-library interactions. This capture and release method may be applied to various assay schemes, not limited to sequencing or targeted assays. An alternative approach can be followed in which sequencing libraries of an entire genome are immobilized on a solid-support, and only the targeted libraries are eluted from the solid-phase.

Certain Methods for Associating Targets and Probes

Some of the methods and compositions provided herein relate to associating target nucleic acids and capture probes, e.g., capture probes comprising hybridization tags. In some embodiments, the target nucleic acid is double stranded. As will be understood, in some embodiments that include hybridizing long nucleic acids comprising targets e.g., genomic DNA, and hybridization tags, the use of double-stranded nucleic acids can minimize non-specific nucleic acid hybridization, e.g., interaction of genomic repetitive elements. Some methods include a step for a hybridization tag to invade a double-stranded target nucleic acid. In some embodiments, a hybridization tag can hybridize to a single-stranded target nucleic acid. Some such methods may include a step to overcome non-specific nucleic acid hybridization, e.g., interaction of genomic repetitive elements. For example, some methods may include rigorous washing of a nucleic acid mixture comprising target nucleic acids hybridized to hybridization tags, and other nucleic acids. In some such embodiments, the target nucleic acid and hybridization tag may be tightly associated with each other by methods described herein.

In some embodiments, a denatured double-stranded nucleic acid e.g., a circular nucleic acid molecule, comprising a target is hybridized to a capture probe comprising a hybridization tag. In some such embodiments, blocking nucleic acids, e.g., 40 nucleotide oligomers directly abut either side of the hybridization tag (See, e.g., Shepard A. R. et al. (1997) "Magnetic bead capture of cDNAs from double-stranded plasmid cDNA libraries." *Nucleic Acids Research* 25:3183-3185, the disclosure of which is incorporated herein by reference in its entirety). The blocking nucleic acids may function to reduce re-zippering of the denatured circular nucleic acid molecule.

In some embodiments, a double-stranded target nucleic acid comprising a triple helix forming sequence can be hybridized to a capture probe comprising a single-stranded hybridization tag. Triple helix forming sequences may be introduced into nucleic acids to create target nucleic acids. Without wishing to be bound by any one theory, local triple helix formation may occur by specific binding at high pH of homopyrimidine single-stranded nucleic acids in the major groove of duplex double-stranded nucleic acids, e.g., DNA, parallel to the purine Watson-Crick strand through the formation of Hoogsteen hydrogen bounds. Triple helix formation can be highly specific to thymine recognition of adenine-thymine base pairs and protonated cytosine recognition of guanine-cytosine base pairs which is reversible when pH is lowered (See, e.g., Sonti S. V. et al., (1995) "Large scale isolation of expression vector cassette by magnetic triple helix affinity capture." *Nucleic Acids Research* 23:3995-3996).

In some embodiments, a capture probe comprising a single-stranded hybridization tag can be hybridized to a double-stranded target nucleic acid using PNA openers. PD-loops can be assembled sequence specifically with the aid of PNAs (See, e.g., Demidov et al., (2000) "Duplex DNA capture." *Curr. Issues Mol. Biol.* 2:31-35, the disclosure of which is incorporated herein by reference in its entirety). Without wishing to be bound by any one theory, formation of the PD-loop may be based on the ability of short homopyrimidine PNAs to displace one strand of double-stranded nucleic acid forming a PNA-NA-PNA triplex with the other strand. This stable structure, known as a P-loop, is formed most readily with the use of positively charged bis-PNA. When a pair of such PNA openers bind to closely located homopurine DNA tracts separated by any short sequence of nucleobases, the two adjacent P-loops merge and an extended open region emerges inside dsDNA. This open region can serve as a target for binding of capture probe comprising a hybridization tag that cannot by itself form stable complexes with linear double-stranded nucleic acid. In some embodiments, a double-stranded nucleic acid comprising a target is denatured, and contacted with PNA openers, and then contacted with capture probe comprising a hybridization tag. The hybridization tag hybridizes to the target nucleic acid.

In some embodiments, proteins that facilitate strand-invasion can be utilized in hybridizing capture probes comprising a hybridization tag to target nucleic acids. In some embodiments, the protein comprises RecA. In an example embodiment, RecA can facilitate triple-helix formation between a single-stranded hybridization tag and a double-stranded target (See, e.g., Hakvoort B. M. et al. (1996), "Preparation of a differentially expressed, full-length cDNA expression library by RecA-mediated triple-strand formation with subtractively enriched cDNA fragments." *Nucleic Acids Research* 24:3478-3480, the disclosure of which is incorporated herein by reference in its entirety).

In some embodiments, a capture probe comprising a single-stranded hybridization tag can be hybridized to the single-stranded end of double-stranded target nucleic acid in which the single-stranded end comprises a target nucleic acid. In some such embodiments, double-stranded target nucleic acid can be cut with restriction endonucleases, e.g., rare cutting endonucleases, which results in nucleic acids with single-stranded ends. The single-stranded ends of the nucleic acids can comprise target nucleic acids. A capture probe comprising a hybridization tag can hybridize to the single-stranded targets. In some embodiments, the capture probe and/or the hybridization probe can comprise RNA (See e.g., Kandpal R. P. et al., (1990) "Selective enrichment of a large size genomic DNA fragment by affinity capture: an approach for genome mapping." *Nucleic Acids Research* 18:1789-1795, the disclosure of which is incorporated herein by reference in its entirety). The use of RNA in various embodiments provided herein can facilitate removal of capture probe from DNA molecules comprising targets.

Hybridizing Capture Probes to Single-Strand Gaps of Target Nucleic Acids

Some methods for selective enrichment of nucleic acids include hybridizing a capture probe to a single-stranded gap in a target double-stranded nucleic acid. The single-strand gap of a double-stranded target nucleic acid can comprise at least a portion of a target. In some embodiments, the target nucleic acid hybridized to a capture probe can be separated from nucleic acids not hybridized to the capture probe using methods and compositions described herein.

In certain embodiments, a double-stranded nucleic acid comprising a single-stranded gap can be generated by contacting a double stranded nucleic acid with a nickase. Nickases include endonucleases that recognize a specific recognition sequence in a double-stranded nucleic acid, and cut one strand at a specific location relative to the recognition sequence, thereby giving rise to single-stranded breaks in the double-stranded nucleic acid. Examples of nickases include Nb.BbvCI, Nb.BsmI, Nb.BsrDI, Nb.BtsI, Nt.AlwI, Nt.BbvCI, Nt.BsmAI, Nt.BspQI, Nt.BstNBI, and Nt.CviPII. Conditions using nickases to generate single-strand breaks in double-stranded nucleic acids, such as DNA, are well known in the art. In further embodiments, a single-strand gap in a double-stranded nucleic acid can be generated by contacting a single-strand gap with an exonuclease having activity at nicks in double-stranded nucleic acids to produce single-strand gaps in a double-stranded nucleic acid. Examples of such exonucleases include Exonuclease III, and T7 Exonuclease. Conditions using exonucleases to generate single-stranded gaps in double-stranded nucleic acids are well known in the art.

Other embodiments of the methods described herein can include pre-treating a population of target nucleic acids with a restriction endonuclease, before contacting the population of target nucleic acids with a nickase. The Type II restriction endonuclease can include an isoschizomer of a nickase. Examples of such isoschizomers include BbvCI, BsmI, BsaMI, BscCI, Mva1269I, PctI, BsrDI, Bse3DI, BseMI, BtsI, AlwI, AclWI, BinI, BspPI, BsmAI, Alw26I, BsoMAI, BstMAI, MlyI, PleI, PpsI, and SchI. In some embodiments, a population of target nucleic acids cut with a restriction endonuclease can be recircularized under conditions that promote intramolecular circularization of target nucleic acids. In some such embodiments, the recognition site of a nickase can be created in the circular target nucleic acids.

Crosslinking Capture Probes and Target Nucleic Acids

Some methods and compositions for the selective enrichment of a nucleic acid can include covalently crosslinking hybridization tags hybridized to target nucleic acids. Crosslinking a capture probe to a target nucleic acid can permit increased hybridization stringency conditions. For example, in some methods that include separating target nucleic acids hybridized to capture probes from nucleic acids not hybridized to capture probe, crosslinking can permit increased stringency in wash conditions.

Crosslinking can be accomplished by a variety of methods. For example, a crosslinking moiety can be used to crosslink a hybridization tag hybridized to a target nucleic acid. In certain embodiments, a hybridization tag can comprise a crosslinking moiety. In one embodiment, the crosslinking moiety can be directly incorporated into the hybridization tag, such as at the time of synthesis using appropriately modified nucleoside or nucleotide derivatives, namely, nucleotide analogs. In other embodiments, a crosslinking moiety can be introduced into a hybridization tag hybridized to a target nucleic acid duplex post-hybridization, for example using soluble derivatives of the crosslinking moiety followed by photochemical or chemical activation. For example, a crosslinking moiety can be introduced by extending a hybridization tag hybridized to a target nucleic acid. In another example, an oligonucleotide comprising a crosslinking moiety can be ligated to a hybridization tag hybridized to a target nucleic acid.

The crosslinking moiety can be any chemical moiety which is capable of forming a covalent crosslink between the hybridization tag and target nucleic acid. For example, the precursor to the crosslinking moiety can optionally be a coumarin, furocoumarin, or benzodipyrone. Crosslinking moieties useful in methods and compositions described herein are known to those skilled in the art. For instance, U.S. Pat. Nos. 4,599,303 and 4,826,967 disclose crosslinking compounds based on furocoumarin useful in methods and compositions described herein. U.S. Pat. No. 5,082,934 describes a photoactivatible nucleoside analogue comprising a coumarin moiety linked through its phenyl ring to a ribose or deoxyribose sugar moiety without an intervening base moiety. In addition, U.S. Pat. No. 6,005,093 describes non-nucleosidic, stable, photoactive compounds that can be used as photo-crosslinking reagents in nucleic acid hybridization assays. These references are incorporated herein by reference in their entirety for at least the teaching of crosslinking moieties.

The precursor of the crosslinking moiety can be a coumarin, 7-hydroxycoumarin, 6,7-dihydroxycoumarin, 6-alkoxy-7-hydroxycoumarin, psoralen, 8-methoxypsoralen, 5-methoxypsoralen, 4,5',8-trimethylpsoralen, 4'-hydroxymethyl-4,5',8-trimethylpsoralen, and 4'-aminomethyl-4,5',8-trimethylpsoralen, a haloalkyl coumarin, a haloalkyl furocoumarin, a haloalkyl benzodipyrone, or a derivative thereof. The crosslinking moiety can be incorporated into a nucleic acid sequence by methods well known in the art. Compounds containing fused coumarin-cinnoline ring systems are also useful in methods and compositions described herein. The crosslinking moiety can be part of a mono-adducted furocoumarin:nucleoside adduct.

The nature of the formation of the covalent bond comprising the crosslink will depend upon the crosslinking moiety chosen. For example, the activation of the covalent bond can occur photochemically, chemically or spontaneously.

A variety of chemistries can be used for covalent crosslinking of DNA strands, including alkylating agents like nitrogen mustard derivatives or ultraviolet light-activated agents like derivatives of psoralen (Denny W A, ed. New developments in the use of nitrogen mustard alkylating agents as anticancer drugs, In "Advances in DNA Sequence-Specific Agents" series, Eds. Graham B. Jones and Manlio Palumbo, v.3, JAI Press 1998, p. 157; Takasugi M, et al. Sequence-Specific Photo-Induced Crosslinking of the Two Strands of Double-Helical DNA by a Psoralen Covalently Linked to a Triple Helix-Forming Oligonucleotide. Proc. Natl. Acad. USA (1991) 88:5602-5606). Both classes can be incorporated into synthetic oligonucleotides which are typically used as anticancer drugs. Sufficient literature exists on photo-activated crosslinkers suitable for a DNA or protein modification. Crosslinkers for this purpose were specially designed to be activated by near UV light (300-400 nm) to prevent damage of biological molecules (in particular DNA) which absorb below this wavelength region. Other methods and compositions for crosslinking nucleic acids are described in U.S. Patent Application Publication No. 20090011514, incorporated herein by reference in its entirety.

Padlock Capture Probes

Some methods and compositions described herein can include capture probes comprising padlock probes. As used herein, the term "padlock probe" and grammatical equivalents can refer to a class of circle probes, comprising a nucleic acid sequence with a free 3'-end and a free 5'-end, which upon hybridization to a target will fold so that the 3'-end and the 5'-end are positioned next to each other, enabling ligation, or extension and ligation, to form a closed circular structure. (U.S. Pat. Nos. 5,871,921; 6,235,472; 5,866,337; and M. Nilsson et al., "Padlock Probes: Circularizing Oligonucleotides for Localized DNA Detection," Science 265: 2085-88 (1994), the disclosures of which are incorporated herein by reference in their entireties). In some embodiments, a padlock probe can be adapted to be circularized in the presence of a target sequence, such that the cyclic probe interlocks with the target nucleic acid. In other words, because of the helical nature of double-stranded nucleic acids, circularized probes will be wound around the target strand, topologically connecting probes to target molecules through catenation. Such covalent catenation of probe molecules to target sequences results in the formation of a hybrid that resists extreme washing conditions, serving to reduce non-specific signals.

Some embodiments include capture probes comprising padlock probes, such as molecular inversion probes (MIPs). MIPs can include a single oligonucleotide probe with hybridization tags, e.g., recognition sequences at each terminus (Hardenbol et al., Genome Res. 15(2):269-275, 2005, Hardenbol, P. et al. Nature Biotechnology 2 1 (6), 673-8, 2003; Faham M, et al. Hum Mol Genet. August 1; 10(16): 1657-64, 2001: Maneesh Jain, Ph.D., et al. Genetic Engineering News V24: No. 18, 2004; and Fakhrai-Rad H, et al. Genome Res. July; 14(7):1404-12, 2004; Porreca, G J et al. Multiplex amplification of large sets of human exons. Nat. Methods. 4, 931-936 (2007); Krishnakumar S, et al. A comprehensive assay for targeted multiplex amplification of human DNA sequences. Proc. Natl. Acad. Sci USA 105, 9296-9301 (2008); and in U.S. Pat. No. 5,858,412, and U.S. Pat. No. 6,858,412, each of which is incorporated herein by reference in its entirety). In some embodiments, the recognition sequences can be hybridized with a genomic target sequence such that a circular structure is formed, with the ends of the probe abutting. This leaves a single base gap at the location of a SNP. This gapped-duplex is then tested in four separate reactions, each with a single dNTP species present, in which successful polymerization/ligation provides allelic differentiation. The probes are subsequently released from the genomic DNA and those that have been covalently circularized in the correct allele/nucleotide reaction combinations are amplified using a "universal" PCR primer pair. Each amplified probe contains a unique tag sequence that is complementary to a sequence on the universal tag array. Tags have been selected to have a similar $T_m$ and base composition and to be maximally orthogonal in sequence complementarity. Amplicons are fluorescently labeled and the tag sequences released from the genome homology regions using a restriction endonuclease treatment. The tags are then detected using a complementary tag array.

Padlock probes can be released from target nucleic acids by a variety of methods. For example, padlock probes comprising RNA may be treated with RNase to release the target nucleic acid from the padlock probe. In more examples, padlock probes may comprise cleavable nucleosides, e.g., dUTP, or cleavable nucleotide analogs that permit release of the padlock probe from the target nucleic acid. In additional examples, a padlock probe can be released from the target nucleic acid with a topoisomerase to unlink a circularized target nucleic acid and a circularized padlock probe.

Selector Capture Probes

Some methods and compositions for selective enrichment of nucleic acids can include capture probes comprising selector probes.

In some embodiments, selector probes comprise hybridization tags, e.g., target-complementary end-sequences, joined by a general linking sequence adapted to ligate templates and to direct circularization of target nucleic acids. In some embodiments, circularized targets can be amplified in multiplex using a primer pair, e.g., an universal PCR primer pair, specific for the general linking sequence in the selectors (Dahl, F et al. (2005) Multiplex amplification enabled by selective circularization of large sets of genomic DNA fragments. Nucleic Acids Res. 33, e71; and Dahl F et al. (2007) Multiplex amplification and massively parallel sequencing for cancer mutation discovery. Proc. Natl. Acad. Sci. USA 104, 9387-9392, the disclosures of which are incorporated herein by reference in their entireties).

Figure 3:
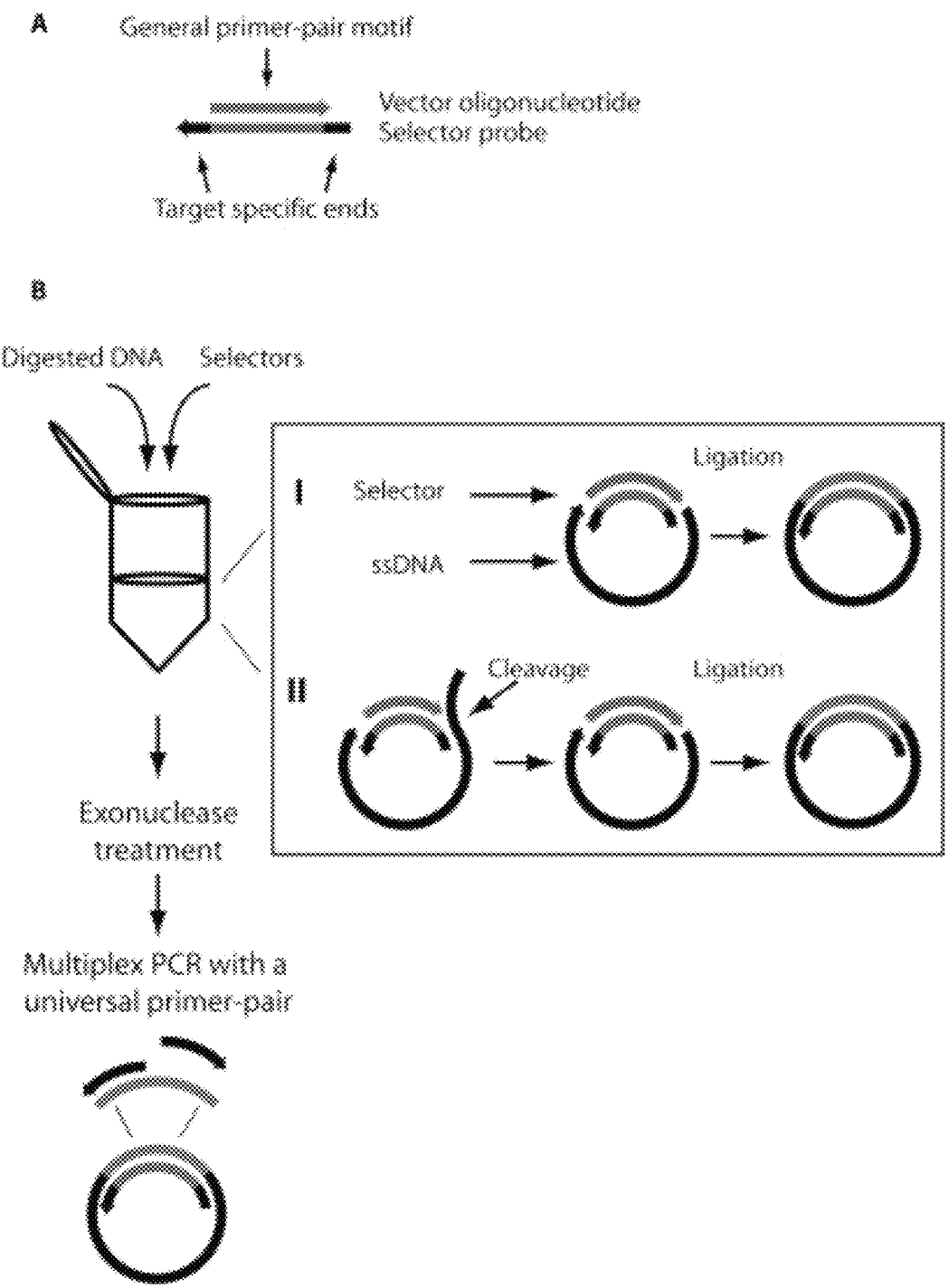
FIG. 3 shows a schematic diagram of an embodiment of a method including a selector probe.

In an exemplary embodiment, a selector probe comprises two oligonucleotides: one selector probe with two end sequences complementary to the target sequence to be selected for amplification, separated by a general primer-pair motif, and a vector oligonucleotide complementary to a general primer-pair motif (FIG. 3).

As a first step in the circularization reaction, the DNA sample is digested by restriction enzymes to generate target fragments with defined ends. The digested DNA sample can be then denaturated to allow the selector to hybridize to the restriction fragments and template ligation to the vector oligonucleotide, forming single-stranded circular DNA molecules. This step can be performed in a least two methods. In a first method the ends of a targeted restriction fragment hybridize to the appropriate selector probe, and the ends become juxtaposed to the vector oligonucleotide guided by the selector probe. Next, a ligase joins the restriction fragment to the vector oligonucleotide generating a circular DNA strand. In a second method, the 3' end segment of the selector probe is designed to hybridize to the 3' end of a targeted restriction fragment as above, but the 5' end segment of the selector probe is designed to hybridize to an internal sequence in the target fragment, forming a branched structure. This structure can serve as substrate for the endonucleolytic activity of Taq polymerase, resulting in an invasive cleavage. The reaction product is then converted to a circular molecule as in the first method. In the procedure outlined in the second method, the 5' end of the target, and also the size of the amplified sequence, can be defined without being limited by the presence of restriction sites. Both procedures require two hybridization and ligation events in order to circularize a target sequence, while the second method also requires an invasive cleavage. These methods provide sufficient specificity to allow analysis of unique sequences in human genomic DNA. In some embodiments, after the circularization reaction, linear sample DNA is degraded by exonucleolysis. In such embodiments, the sample is enriched for circularized DNA fragments, having the general vector oligonucleotide inserted. These fragments can be amplified in a PCR using a universal primer pair specific for the vector oligonucleotide.

In some embodiments, each target-complementary end-sequence can have a different annealing temperature, namely, different $T_m$ values. Methods to design nucleotide sequences with different $T_m$ values are well known and can include modulating the lengths of a complementary sequence, and modulating the particular nucleotides present in the sequence, e.g., A:T, or G:C, or nucleotide analogs. For example, longer complementary sequences can have higher $T_m$ values than shorter sequences, and sequences comprising a greater content of nucleotides such as G and C nucleotides can have greater $T_m$ values than sequences with a lower content of G and C nucleotides.

Normalizing Amplified Products

Figure 4:
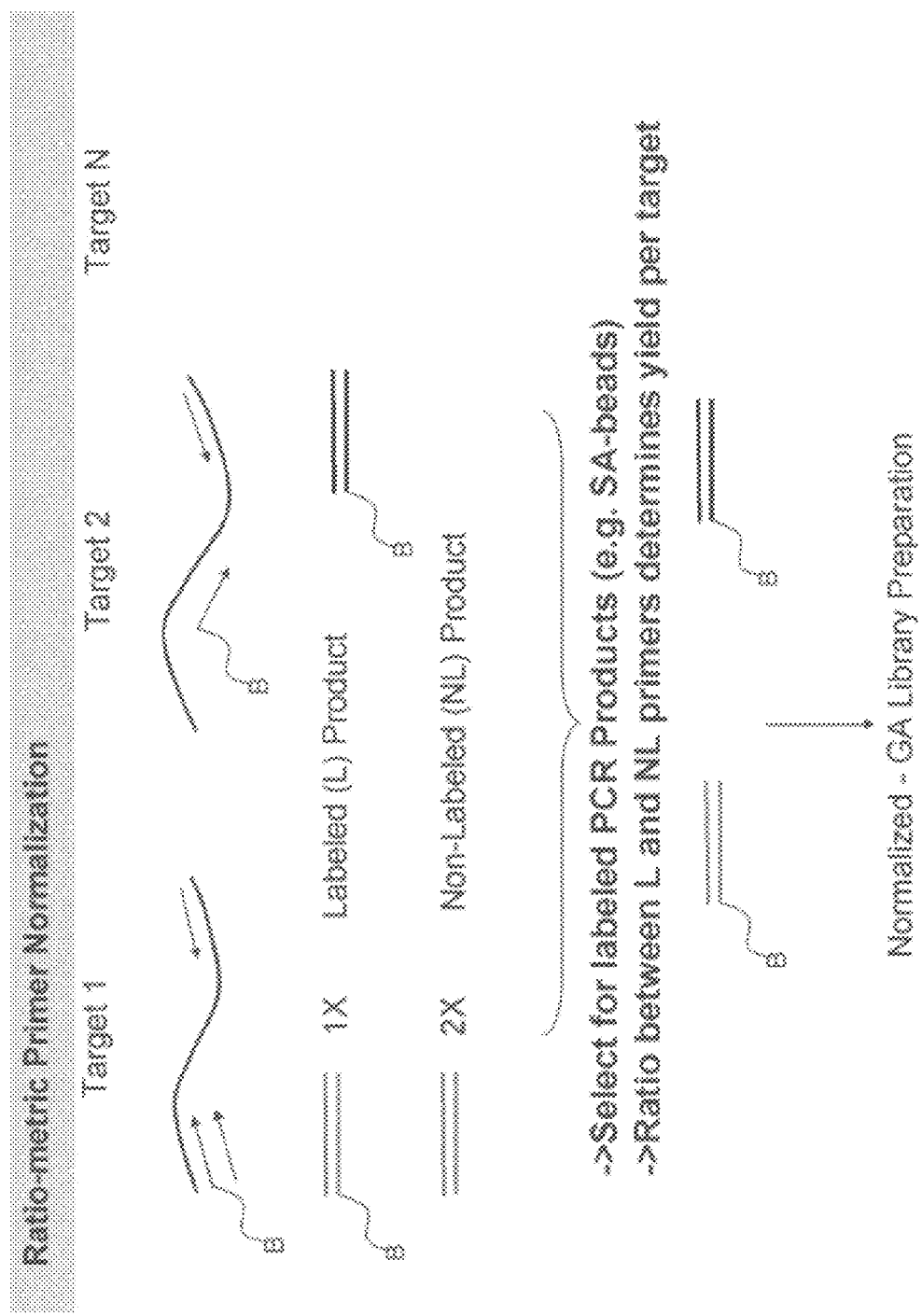
FIG. 4 shows a schematic diagram of an embodiment that includes a multiplex PCR on two targets (Target 1 and Target 2).

Some methods and compositions provided herein can include enriching amplified nucleic acids. As will be understood, although PCR-based methods can be highly specific, some methods suffer from uniformity issues across various target sites. Consequently, variations in several amplified products representing a particular nucleic acid region e.g., genomic DNA region, are observed in PCR-based techniques, e.g., targeted sequencing. Some embodiments herein include the use of a specific ratio of capture probes comprising hybridization tags with and without affinity tags. In a PCR in which hybridization tags are incorporated into a PCR product, the ratio between capture probes comprising an affinity tag and those lacking an affinity tag can determine the fraction of PCR products comprising an affinity tag. PCR products comprising an affinity tag can be separated from other PCR products. As will be understood such methods can be used to normalize particular PCR products in a multiplex reaction. FIG. 4 shows an example embodiment that includes a multiplex PCR on Target 1 and Target 2.

Certain Methods for Enriched Nucleic Acids

Some embodiments include further processing of enriched nucleic acids. In some embodiments, enriched long nucleic acids can be used to prepare libraries for nucleic acid sequencing. In some such embodiments, enriched nucleic acids may be amplified. Some methods of amplification can include circularizing enriched nucleic acids. As will be understood, circularization of either single-stranded or double stranded enriched nucleic acids can provide efficient and unbiased amplification. A circularization step can include ligating a nucleic acid molecule with a ligase such as CircLigase™ (ssDNA), TSSS ligase (ssDNA), T4 ligase (dsDNA), E. coli DNA ligase (dsDNA). In some embodiments, the circularization reaction can be performed in dilute nucleic acid concentrations to reduce the likelihood of interlinking of circles and also concatenation. Circular nucleic acid molecules can be amplified by a variety of methods, for example, rolling circle replication.

Certain Kits

Some embodiments of the present invention include kits for the enrichment of long nucleic acids. Some such kits can include one or more of the following components: (1) one or more capture probes further comprising a hybridization target and affinity tag; (2) reagents for nucleic acid preparation from a biological sample (e.g., lysis buffer and neutralization buffer); (3) a substrate to which the affinity tag may bind (e.g., streptavidin-coated beads); (4) wash buffers; (5) ligase for circularizing nucleic acids; (6) primers for circle-dependent replication; (7) dNTPs for nucleic acid amplification; and (8) a polymerase for circle-dependent replication.

EXAMPLES

Example 1—Association of Capture Probes to Nicked dsDNA

Figure 5:
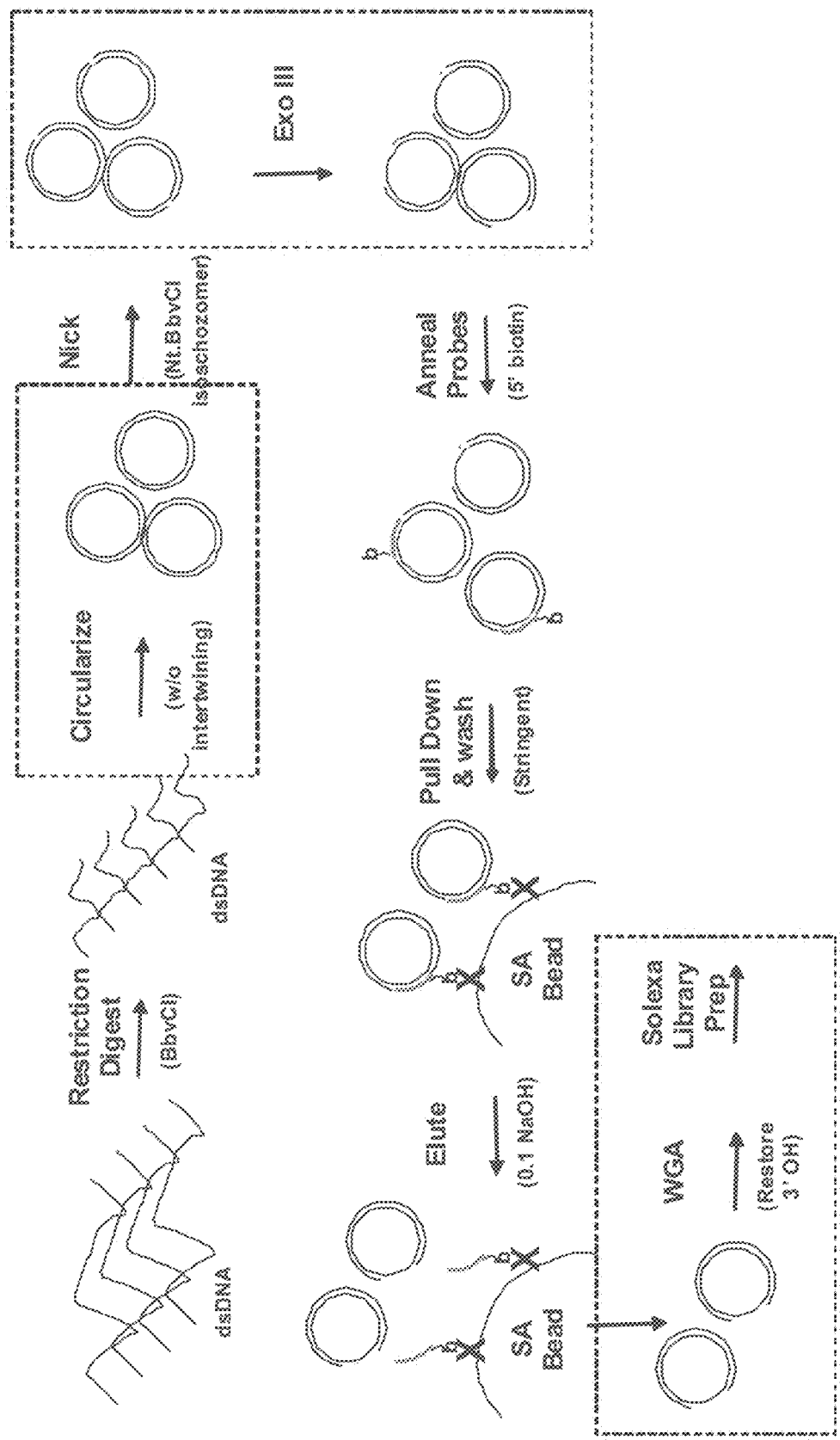
FIG. 5 shows a schematic diagram of an embodiment that includes an association of capture probes to nicked dsDNA.

Double stranded genomic DNA is digested with the endonuclease, BbvCI. The digested DNA is circularized at a dilute DNA concentration to reduce the likelihood that the circular DNA becomes interlinked or concatamerized. The circularized DNA molecules are nicked with the nickase, Nt.BbvCK, an isoschizomer of BbvCI. The nicks are recessed with Exonuclease III under controlled conditions to expose a single-strand region of the circular DNA molecule of about 100-200 bases. Capture probes comprising hybridization tags anneal to the complementary portion of the single-stranded region of the circular DNA molecules. Biotin affinity moieties of the capture probes bind to streptavidin bound to beads. The beads are washed and unassociated nucleic acids are stringently washed from the beads. The washed nucleic acids are eluted from the beads. The nucleic acids are amplified using methods for whole genome amplification e.g., phi29 multiple displacement amplification. The amplified nucleic acids are transformed into a sequencing library, e.g., a SOLEXA library. FIG. 5 shows a schematic diagram summarizing a method that includes associating capture probes to nicked dsDNA. TABLE 1 shows the recognition sites and cut sites for the enzymes BbvCI, Nb.BbvCI, and Nt.BbvCI.

TABLE 1

| Enzyme   | Sequence        | Cut site                        | Overhang |
|----------|-----------------|---------------------------------|----------|
| Nb. BbvCI | C C T C A G C | C C T C A G C<br>G G A G T/C G | Nick     |
| BbvCI    | C C T C A G C   | C C/T C A G C<br>G G A G T/C G | 5'-TCA   |
| Nt. BbvCI | C C T C A G C | C C/T C A G C<br>G G A G T C G | Nick     |

Example 2—Association of a Selector Capture Probe with ssDNA

Figure 6:
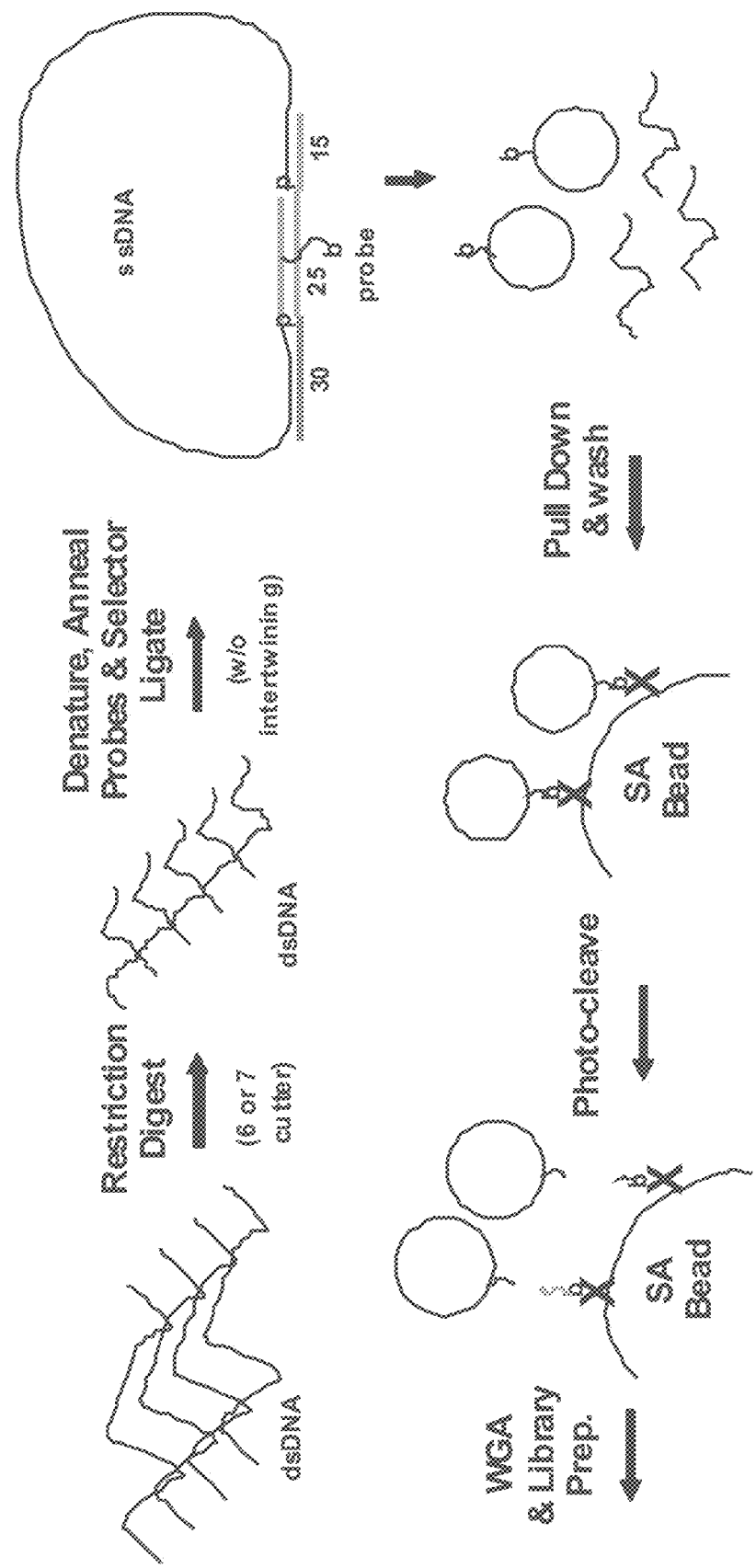
FIG. 6 shows a schematic diagram of an embodiment that includes an association of a selector capture probe with ssDNA.

Double-stranded genomic DNA is restricted with an endonuclease, e.g., an endonuclease with a 6- or 7-base recognition site. The dsDNA is denatured to ssDNA, selector probes anneal to target sequences at each end of the ssDNA. A selector probe pair is designed such that one arm of the selector probe targets one end of a targeted restriction fragment and the other arm targets the other end. The selector probe is ligated to the ssDNA. Biotin affinity moieties of the capture probes bind to streptavidin bound to beads. The beads are washed and unassociated nucleic acids are stringently washed from the beads. The washed nucleic acids are eluted from the beads. The nucleic acids are amplified using methods for whole genome amplification. FIG. 6 summarizes an embodiment that includes the association of a selector capture probe with ssDNA.

Example 3—Association of a Selector Capture Probe with dsDNA

Figure 7:
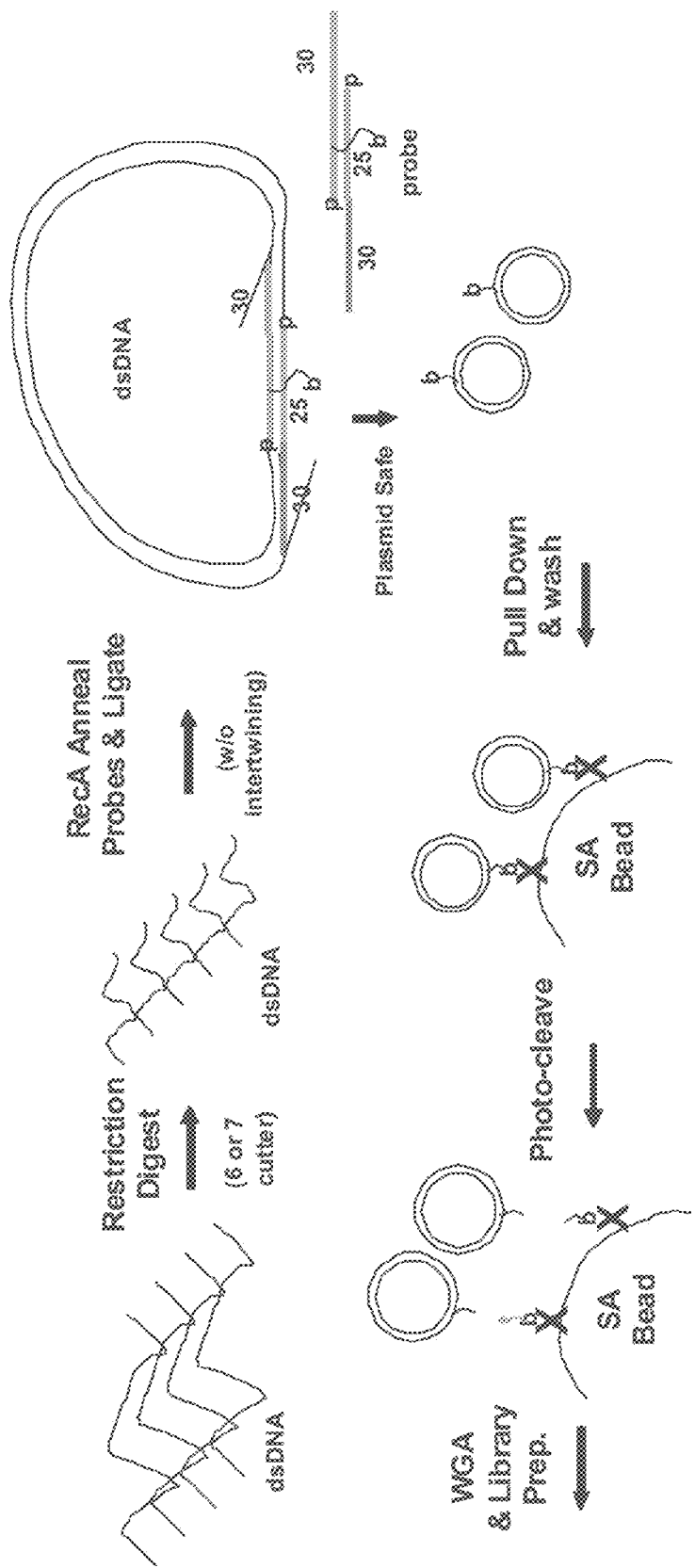
FIG. 7 shows a schematic diagram of an embodiment that includes an association of a selector capture probe with dsDNA.

Double-stranded genomic DNA is restricted with an endonuclease, e.g., an endonuclease with a 6- or 7-base recognition site. The dsDNA is contacted with RecA and a selector probe. RecA facilitates strand invasion of the selector probe into the ends of the dsDNA, and permits the selector probe to anneal to target sequences at each end of the dsDNA. The selector probe is ligated to the dsDNA. The overhang is removed with a FLAP endonuclease. Biotin affinity moieties of the capture probes bind to streptavidin bound to beads. The beads are washed and unassociated nucleic acids are stringently washed from the beads. The washed nucleic acids are eluted from the beads. The nucleic acids are amplified using methods for whole genome amplification. FIG. 7 summarizes an embodiment that includes the association of a selector capture probe with dsDNA.

Example 4—Association of a Cross-Linkable Probe with Target Nucleic Acids

Figure 8:
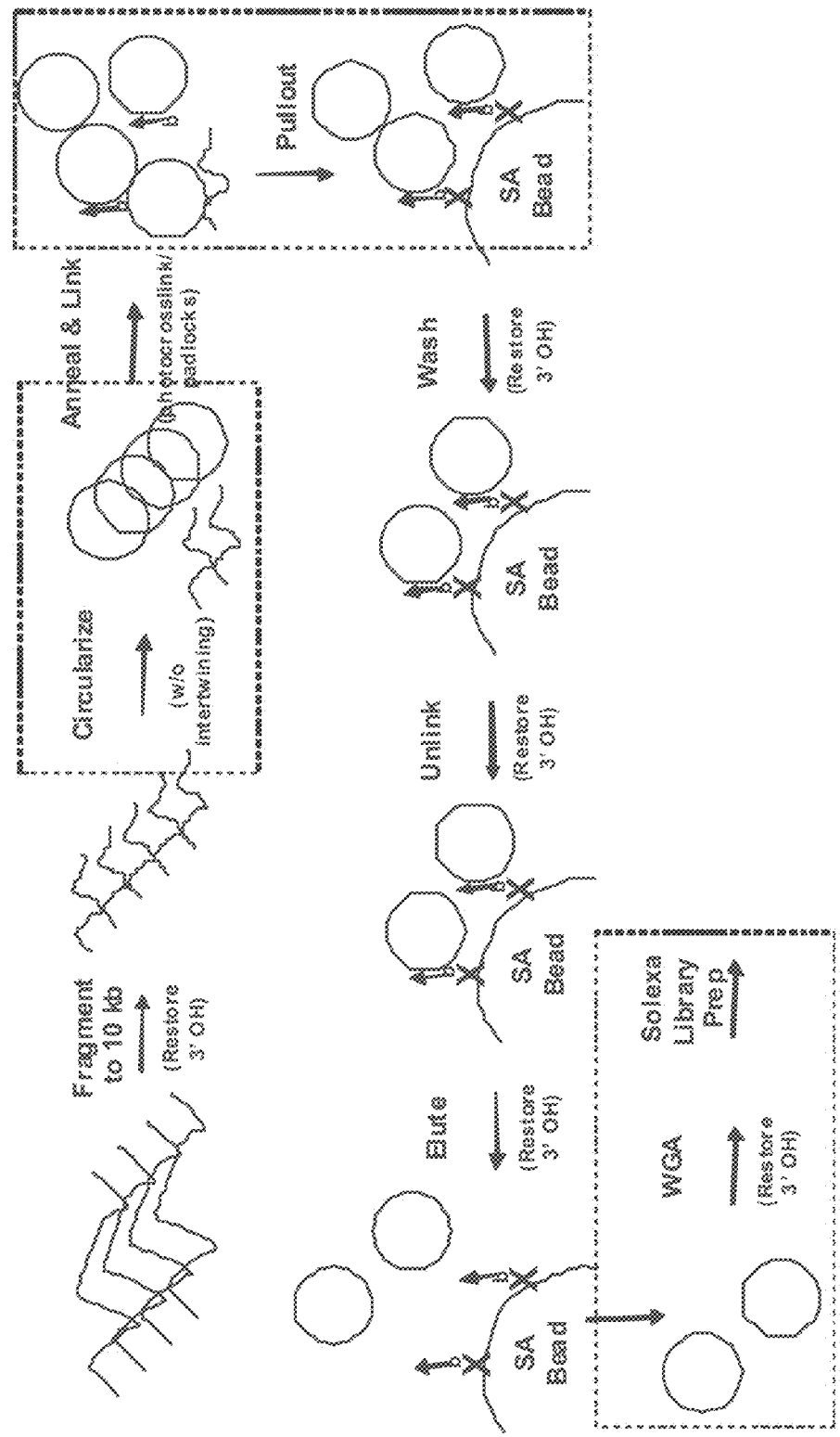
FIG. 8 shows a schematic diagram of an embodiment that includes an association of a cross-linkable probe with target nucleic acids.

Double stranded genomic DNA is fragmented to an average size of 10 kb. The DNA is circularized at a dilute DNA concentration to reduce the likelihood that the circular DNA becomes interlinked or concatamerized. A capture probe comprising a hybridization tag is crosslinked to a target nucleic acid using psoralen. Biotin affinity moieties of the capture probes bind to streptavidin bound to beads. The beads are washed and unassociated nucleic acids are stringently washed from the beads. The circular DNA comprising target nucleic acids are unlinked from the capture probes by cleavage of a cleavable moiety in the capture probes. Examples of cleavable moieties include dUTP, RNA capture probes that may be digested with RNAse. The nucleic acids are amplified using methods for whole genome amplification e.g., phi29 multiple displacement amplification. The amplified nucleic acids are transformed into a sequencing library, e.g., a SOLEXA library. FIG. 8 shows a schematic diagram summarizing a method that includes associating capture probes to nicked dsDNA.

Figure 9:
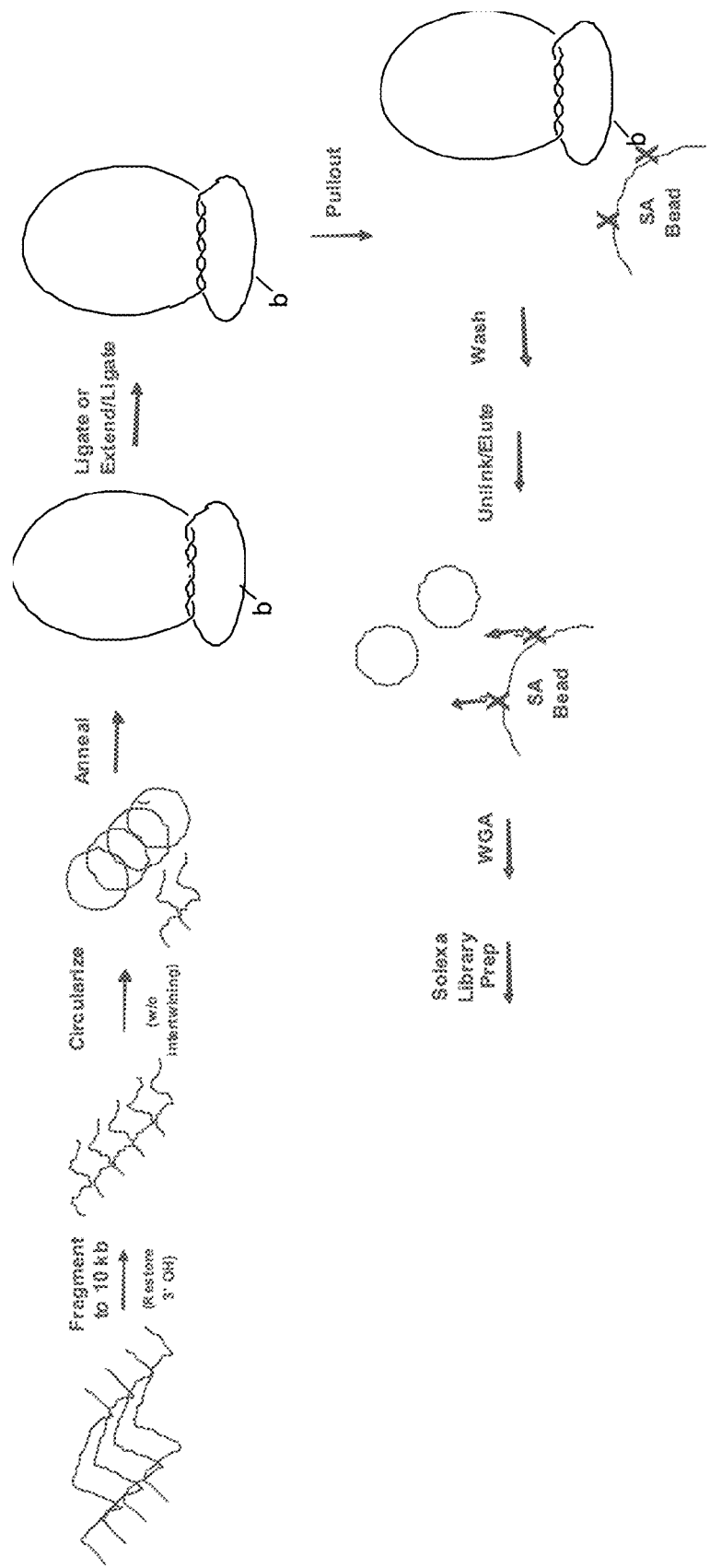
FIG. 9 shows a schematic diagram of an embodiment that includes an association of a capture probe and target nucleic acids by topological linking.

Example 5—Association of a Capture Probe and Target Nucleic Acids by Topological Linking Double stranded genomic DNA is fragmented to an average size of 10 kb. The DNA is circularized at a dilute DNA concentration to reduce the likelihood that the circular DNA becomes interlinked or concatamerized. A capture probe is designed so that a loop is formed between the capture probe and the circular DNA containing targeted nucleic acids. The capture probe anneals to target nucleic acids and the ends of the capture probe are extended and ligated to form an interlocking capture probe and circular DNA comprising target nucleic acids. Biotin affinity moieties of the capture probes bind to streptavidin bound to beads. The beads are stringently washed and unassociated nucleic acids are removed from the beads. The circular DNA comprising target nucleic acids are unlinked from the capture probes by cleavage of a cleavable moiety in the capture probes. Examples of cleavable moieties include dUTP, RNA capture probes that may be digested with RNAse. The nucleic acids are amplified using methods for whole genome amplification e.g., phi29 multiple displacement amplification. The amplified nucleic acids are transformed into a sequencing library, e.g., a SOLEXA library. FIG. 9 shows a schematic diagram summarizing a method that includes associating capture probes to target nucleic acids by topological linking.

Example 6—Targeted Sequencing of BRCA2

Genomic DNA comprising BRCA2 was sequenced using a sequencing library that had undergone a single round of enrichment, and a sequencing library that had undergone two rounds of enrichment. Using the sequencing library that had undergone a single round of enrichment, a 40% enrichment and a readcount distribution ~9× for >90% probes was obtained. Using the sequencing library that had undergone a two rounds of enrichment, a 60-80% enrichment with a readcount distribution of ~13× for >90% of the probes was obtained.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for selective enrichment of a nucleic acid, said method comprising the steps of:
   (a) obtaining a population of nucleic acids, wherein at least some of the nucleic acids in said population comprise a target;
   (b) hybridizing said target with a capture probe;
   (c) locking said hybridized capture probe to said target; and
   (d) separating a nucleic acid locked to the capture probe from a nucleic acid that is not locked to a capture probe.

2. The method of claim 1, wherein said locking comprises contacting psoralen to said capture probe hybridized to said target.

3. The method of claim 1, wherein said target comprises a 5' portion and a 3' portion, and wherein said capture probe comprises a first end complementary to at least a portion of said 5' portion of said target, an intermediary region, and a second end complementary to at least a portion of said 3' portion of said target; and wherein said locking comprises joining together the first end to the second end of said capture probe, thereby locking said capture probe to said target.

4. The method of claim 3, wherein said joining comprises extending and ligating the first end to the second end of said capture probe.

5. The method of claim 4, wherein said extending incorporates a capture moiety into said capture probe.

6. The method of claim 1, wherein said population comprises circularized nucleic acids.

7. The method of claim 1, further comprising repeating steps (a)-(d).

8. The method of claim 1, wherein said target comprises a first capture moiety, and said capture probe comprises a second capture moiety, the method further comprising:

contacting said first capture moiety to a first binding moiety, thereby enriching for said target, and contacting said second capture moiety to a second binding moiety, thereby enriching for said capture probe.

9. A method for selective enrichment of a nucleic acid, said method comprising the steps of:
   (a) obtaining a population of nucleic acids, wherein at least some of the nucleic acids in said population comprise a target, said target comprising a portion of the 5' end of a nucleic acid and a portion of the 3' end of the nucleic acid;
   (b) obtaining a selector probe comprising a first and second oligonucleotide annealed together, wherein said first oligonucleotide is complementary to at least a portion of said 5' end of the nucleic acid and complementary to at least a portion of said second oligonucleotide, and said second oligonucleotide is complementary to at least a portion of said 3' end of the nucleic acid;
   (c) contacting said selector probe to said target, wherein said selector probe hybridizes to said target;
   (d) joining said selector probe hybridized to said target; and
   (e) separating a nucleic acid joined to said selector probe from a nucleic acid not joined to a selector probe.

10. The method of claim 9, further comprising sequencing at least a portion of said target.

11. The method of claim 9, wherein said contacting comprises contacting said selector probe and target with Rec A.

12. The method of claim 9, wherein said separating further comprises contacting a binding moiety to said selector probe joined to said target.

13. The method of claim 9, further comprising repeating steps (a)-(e).

14. The method of claim 9, wherein said target comprises a first capture moiety, and said selector probe comprises a second capture moiety, the method further comprising
   contacting said first capture moiety to a first binding moiety, thereby enriching for said target, and
   contacting said second capture moiety to a second binding moiety, thereby enriching for said selector probe.

15. A method for selective enrichment of a nucleic acid, said method comprising the steps of:
   (a) obtaining a population of single-stranded nucleic acids, wherein at least some of the nucleic acids in said population comprise a target, said target comprising the 5' end of a nucleic acid and the 3' end of the nucleic acid;
   (b) obtaining a selector probe comprising a first and second oligonucleotide annealed together, wherein said first oligonucleotide comprises a 5' portion complementary to said 3' end of the nucleic acid, a spacer portion, and a 3' portion complementary to said 5' end of the nucleic acid, said second oligonucleotide being complementary to said spacer portion;
   (c) contacting said selector probe to said target, wherein said selector probe hybridizes to said target;
   (d) joining said selector probe hybridized to said target; and
   (e) separating a nucleic acid joined to said selector probe from a nucleic acid not joined to a selector probe;
   wherein said target comprises a first capture moiety, and said selector probe comprises a second capture moiety, the method further comprising:
   contacting said first capture moiety to a first binding moiety, thereby enriching for said target, and contacting said second capture moiety to a second binding moiety, thereby enriching for said selector probe.

16. The method of claim 15, wherein a 5' end and a 3' end of the selector probe have different annealing temperatures from one another.

17. The method of claim 15, further comprising sequencing at least a portion of said target.

18. The method of claim 15, further comprising repeating steps (a)-(e).

19. A method for normalizing amplified nucleic acids comprising:
   (a) selecting a first population of oligonucleotides capable of hybridizing to a first target, wherein the first population of oligonucleotides comprises oligonucleotides comprising capture moieties and oligonucleotides lacking capture moieties;
   (b) obtaining a second population of oligonucleotides capable of hybridizing to a second target, wherein the second population of oligonucleotides comprises oligonucleotides comprising capture moieties;
   (c) amplifying first and second target nucleic acids with said first and second populations of oligonucleotides; and
   (d) separating amplified targets having incorporated oligonucleotide comprising capture moieties from amplified targets lacking incorporated oligonucleotide capture moieties, thereby obtaining a population of normalized amplified nucleic acids comprising capture moieties.

* * * * *

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: c-myc epitope tag

<400> SEQUENCE: 1

Glu Gln Lys Leu Ile Ser Glu Glu Asp Leu
1               5                   10

<210> SEQ ID NO 2
<211> LENGTH: 9
<212> TYPE: PRT
<213> ORGANISM: Artificial Sequence
<220> FEATURE:
<223> OTHER INFORMATION: viral HA protein epitope tag
```

```
<400> SEQUENCE: 2

Tyr Pro Tyr Asp Val Pro Asp Tyr Ala
 1               5

<210> SEQ ID NO 3
<211> LENGTH: 11
<212> TYPE: PRT
<213> ORGANISM: Artificial Sequence
<220> FEATURE:
<223> OTHER INFORMATION: VSV-G epitope tag

<400> SEQUENCE: 3

Tyr Thr Asp Ile Glu Met Asn Arg Leu Gly Lys
 1               5                   10

<210> SEQ ID NO 4
<211> LENGTH: 11
<212> TYPE: PRT
<213> ORGANISM: Artificial Sequence
<220> FEATURE:
<223> OTHER INFORMATION: viral HSV epitope tag

<400> SEQUENCE: 4

Gln Pro Glu Leu Ala Pro Glu Asp Pro Glu Asp
 1               5                   10

<210> SEQ ID NO 5
<211> LENGTH: 14
<212> TYPE: PRT
<213> ORGANISM: Artificial Sequence
<220> FEATURE:
<223> OTHER INFORMATION: viral V5 epitope tag

<400> SEQUENCE: 5

Gly Lys Pro Ile Pro Asn Pro Leu Leu Gly Leu Asp Ser Thr
 1               5                   10

<210> SEQ ID NO 6
<211> LENGTH: 9
<212> TYPE: PRT
<213> ORGANISM: Artificial Sequence
<220> FEATURE:
<223> OTHER INFORMATION: epitope tag

<400> SEQUENCE: 6

Asp Tyr Lys Asp Asp Asp Asp Lys Gly
 1               5
```